(12) United States Patent
Dunham

(10) Patent No.: US 11,834,657 B2
(45) Date of Patent: Dec. 5, 2023

(54) METHODS FOR SAMPLE PREPARATION

(71) Applicants: University of Southern California, Los Angeles, CA (US); SeqOnce Biosciences Inc., La Canada-Flintridge, CA (US)

(72) Inventor: Joseph Dunham, El Segundo, CA (US)

(73) Assignees: University of Southern California, Los Angeles, CA (US); SeqOnce Biosciences Inc., La Canada-Flintridge, CA (US)

( * ) Notice: Subject to any disclaimer, the term of this patent is extended or adjusted under 35 U.S.C. 154(b) by 410 days.

(21) Appl. No.: 16/006,354

(22) Filed: Jun. 12, 2018

(65) Prior Publication Data

US 2019/0048334 A1 Feb. 14, 2019

Related U.S. Application Data

(63) Continuation of application No. 14/691,457, filed on Apr. 20, 2015, now abandoned.

(60) Provisional application No. 62/054,886, filed on Sep. 24, 2014.

(51) Int. Cl.
*C12N 15/10* (2006.01)
*C40B 50/06* (2006.01)

(52) U.S. Cl.
CPC .......... *C12N 15/1093* (2013.01); *C40B 50/06* (2013.01)

(58) Field of Classification Search
CPC ...... C12N 15/10; C12N 15/1093; C12N 9/14; C12N 9/93; C40B 40/06; C40B 50/06; B01J 2219/00722; B01J 2219/00585
See application file for complete search history.

(56) References Cited

U.S. PATENT DOCUMENTS

| | | | |
|---|---|---|---|
| 5,935,793 A | 8/1999 | Wong | |
| 8,673,560 B2 | 3/2014 | Leamon et al. | |
| 8,728,728 B2 | 5/2014 | Leamon et al. | |
| 8,728,736 B2 | 5/2014 | Leamon et al. | |
| 2006/0040282 A1 | 2/2006 | Monforte et al. | |
| 2009/0068645 A1 | 3/2009 | Sibson | |
| 2012/0237943 A1 | 9/2012 | Soldatov et al. | |
| 2012/0295819 A1 | 11/2012 | Leamon et al. | |
| 2013/0059738 A1 | 3/2013 | Leamon et al. | |
| 2013/0059762 A1 | 3/2013 | Leamon et al. | |
| 2013/0231253 A1 | 9/2013 | Amorese et al. | |
| 2015/0038342 A1 | 2/2015 | Leamon et al. | |
| 2015/0038343 A1 | 2/2015 | Leamon et al. | |
| 2015/0038375 A1 | 2/2015 | Leamon et al. | |
| 2015/0203906 A1 | 7/2015 | Betts et al. | |

FOREIGN PATENT DOCUMENTS

| | | |
|---|---|---|
| WO | 2012/149438 A1 | 11/2012 |
| WO | 2013/081755 A1 | 6/2013 |
| WO | 2013/081864 A1 | 6/2013 |

OTHER PUBLICATIONS

Potenza et al. Nucleic Acids Research, 2006, vol. 34(10): 2906-2913, doi:10.1093/nar/gkl368 (Year: 2006).*
Odelberg et al. "Template-switching during DNA synthesis by Thermus aquaticus DNA polymerase I." Nucleic acids research vol. 23,11 (1995): 2049-57. doi:10.1093/nar/23.11.2049 (Year: 1995).*
Zhou et al. "Universal TA Cloning" Curr. Issues Mol. Biol. 2000, 2(1), 1-7; https://doi.org/10.21775/cimb.002.001 (Year: 2000).*
Park et al. "Improvement of the 3'-5' Exonuclease Activity of Taq DNA Polymerase by Protein Engineering in Active-Site" Mol. Cells 1997; 7(3): 419-424 (Year: 1997).*
"Paired-End Sample Preparation Guide", Illumina Proprietary, Feb. 2011, pp. 1-40.
Broad Institute et al., "Sample Preparation Module 1: Overview", 2010, pp. 1-76.
Dobosy et al., "RNase H-dependent PCT (rhPCR): improved specificity and single nucleotide polymorphism detection using blocked cleavable primers", BMC Biotechnology, Biomed Central Ltd. London, GB, vol. 11. No. 1, Aug. 2011, pp. 1-18.
Parkhomchuk et al., "Transcrptome analysis by strand-specific sequencing of complementary DNA", Nucleic Acids Research, 2009, 37(18): e123.
The University of Tokyo Life Science web textbook, 2010, http://csls-text.c.u-tokyo.ac.jp (4 pages).
Examination in Application No. 15845141.9, dated May 7, 2018.
Supplementary European Search Report in Application No. 15845141.9. dated May 7, 2018.
International Search Report and Written Opinion in International Application No. PCT/US15/51947, dated Feb. 9, 2016.

\* cited by examiner

*Primary Examiner* — Kaijiang Zhang
(74) *Attorney, Agent, or Firm* — RAPHAEL BELLUM PLLC

(57) ABSTRACT

The disclosure provides for single amplification and double amplification methods for preparing nucleic acid samples for sequencing.

7 Claims, 18 Drawing Sheets

METHODS FOR SAMPLE PREPARATION

CROSS-REFERENCE TO RELATED APPLICATIONS

The present application claims the benefit of priority to U.S. Provisional Ser. No. 62/054,886, filed Sep. 24, 2014, which is hereby incorporated by reference in its entirety.

STATEMENT AS TO FEDERALLY SPONSORED RESEARCH

This invention was made with government support under GM098741 awarded by National Institutes of Health. The government has certain rights to this invention.

BACKGROUND

Although the cost of nucleic acid sequencing has dropped in recent years, sample preparation remains expensive. There are only a few methods of sample preparation compatible with the most popular sequencing platforms. These methods can be expensive and time consuming. In particular, library preparation can require the generation of overhanging bases on nucleic acid fragments. This step is one of the less efficient steps of preparing sequencing libraries. Improving the efficiency of this step would reduce the amount of starting nucleic acids required to prepare a sequencing library. New methods in sample preparation for sequencing are needed, particularly ones that increase the efficiency by which nucleic acid fragments with overhanging bases are generated.

SUMMARY

Provided herein are methods for generating adaptor-ligated libraries of nucleic acid fragments. In particular, methods are disclosed for preparing partially complementary double-stranded nucleic acid fragments, such that one strand extends past the other to create an overhang. Such overhangs can improve the efficiencies of enzymatic and biochemical reactions. For example, such overhangs can be annealed to their complementary sequence, allowing the targeted pairing of nucleic acid fragments. In another example, ligation of nucleic acid fragments with complementary overhangs is more efficient than ligation of blunt-end nucleic acid fragments.

In one aspect, the disclosure provides for a method for generating an adaptor-ligated library of double-stranded nucleic acid molecules comprising: in a single reaction vessel or reaction mixture, contacting a plurality of single-stranded polynucleotides with a first set of random primers, each random primer comprising a cleavable 5' end; extending the first set of random primers to generate first extension products hybridized to the single-stranded polynucleotides, thereby forming first double-stranded duplexes; denaturing the first double-stranded duplexes into single strands; hybridizing the first polynucleotide extension products with a second set of random primers (the first set and the second set of primers can be the same or different); extending the second set of random printers to generate second extension products hybridized to the first extension products, thereby forming second double-stranded duplexes; cleaving the cleavable 5' ends of the first extension products and/or the second extension products, thereby forming second double-stranded duplexes having one or more overhangs; and ligating one or more double stranded adapters comprising a 3' overhang to the second double-stranded duplexes of the previous step, thereby forming the adaptor-ligated library. The double stranded adapters can in some examples include nucleic acid barcodes, such as sample barcodes, molecular barcodes, or randomizer barcodes. A random primer can be fully degenerate or partially degenerate. The entire library preparation can be performed with a single clean up step. The entire library preparation can be performed with no more than two clean up steps. The entire library preparation can be performed with only three clean up steps.

In some embodiments, the single-stranded polynucleotide is ssDNA. In some embodiments, the single-stranded polynucleotide is RNA. In some embodiments, the primers are random, such as random hexamers. In some embodiments, the primers are a length from 4 to 30 nucleotides in length. In some embodiments, the cleavable 5' end is cleavable by photocleaving. In some embodiments, the cleavable 5' end is cleavable by a nuclease. In some embodiments, the nuclease is an exonuclease. In some embodiments, the nuclease is an endonuclease. In some embodiments, the nuclease is an RNA nuclease. In some embodiments, the nuclease is a DNA nuclease. In some embodiments, the nuclease is a nuclease that can cleave a DNA-RNA hybrid molecule. In some embodiments, the nuclease is a nuclease that cleaves the RNA component of a DNA-RNA hybrid molecule, such as RNaseH. In some cases, the exonuclease activity is provided by the 5'-3' exonuclease activity of a polymerase, such as DNA Polymerase I. In some cases, the nuclease specifically cleaves dU, such as uracil-DNA glycosylase. In some embodiments, the cleavable 5' end comprises a modification selected from the group consisting of: a fluorophore, a dideoxynucleotide, a deoxynucleotide, a radiolabel, a dye, dUTP, rA, rU, rG, rC, rUTP, and a restriction enzyme target sequence, or any combination thereof. In some embodiments, the cleavable 5' end comprises a dUTP. In some embodiments, the cleavable 5' end comprises a rUTP. In some embodiments, the cleavable 5' end is from 1-5 nucleotides. In some embodiments, the cleavable 5' end is 1 nucleotide. In some embodiments, the cleaving removes between 1-5 nucleotides of the primers. In some embodiments, the cleaving removes one or more nucleotide from the primers. In some embodiments, the cleaving comprises cleaving one or more bases. In some embodiments, the one or more overhangs comprises a thymine. In some embodiments, the one or more overhangs comprises an adenine. In some embodiments, one or more overhangs comprises a guanine. In some embodiments, the one or more overhangs comprises a cytosine. In some embodiments, the one or more overhangs comprises a thymine and the 3' overhang comprises an adenine. In some embodiments, the one or more overhangs comprises from 1-5 nucleotides. In some embodiments, the one or more overhangs comprises 1-5 nucleotides of a modification selected from the group consisting of: a fluorophore, a dideoxynucleotide, a deoxynucleotide, a radiolabel, a dye, dUTP, rA, rU, rG, rC, rUTP, and a restriction enzyme target sequence, or any combination thereof. In some embodiments, the extending steps (for example, using dNTP's, dNTP's containing dUTP, rA, rU, rG, rC, rUTP, a fluorophore, a dideoxynucleotide, a deoxynucleotide, a radiolabel, or a dye for downstream purification or degradation) result in a blunt end. In some embodiments, the adapter comprises a sequencing adapter. In some embodiments, the adapter comprises a nucleic acid barcode. In some embodiments, the adapter comprises a nucleic acid barcode sequence. The adapter-ligated library can, in some cases, be sequenced. In some embodiments, the polynucleotide is an ancient polynucleotide. In some embodiments, the polynucleotide is present in 10 or fewer copies. In some embodiments, the method is performed two or more times. The entire library preparation can be performed with a single clean up step. The entire library preparation can be performed with no more than two clean up steps. The entire library preparation can be performed with only three clean up steps.

In one aspect the disclosure provides for a method for generating an adaptor-ligated library of double-stranded nucleic acid molecules comprising: in a single reaction vessel or reaction mixture; contacting a plurality of single-stranded polynucleotides with a first set of target-specific primers, each comprising a cleavable 5' end; extending the first set of primers (e.g., using dNTP's, dNTP's containing dUTP, rA, rU, rG, rC, rUTP, a fluorophore, a dideoxynucleotide, a deoxynucleotide, a radiolabel, or a dye for downstream purification or degradation) to generate first extension products hybridized to the single-stranded polynucleotides, thereby forming first double-stranded duplexes; denaturing the first double-stranded duplexes into single strands; hybridizing the first polynucleotide extension products with a second set of target-specific primers (the first and second set of primers can be the same or different; for example, a first set of primers can specifically hybridize the target nucleic acids (or upstream thereof). The second set of primers can specifically hybridize to a sequence complementary of the target nucleic acids or upstream thereof); extending the second set of primers to generate second extension products hybridized to the first extension products, thereby forming second double-stranded duplexes; cleaving the cleavable 5' ends of the first extension products and/or the second extension products, thereby forming second double-stranded duplexes having one or more overhangs; and ligating one or more double stranded adapters comprising a 3' overhang to the second double-stranded duplexes of the previous step, thereby forming the adaptor-ligated library wherein the method comprises only two steps of extending. The double stranded adapters can include e.g. a nucleic acid barcode, such as a sample barcode, molecular barcode, or randomized barcode. The entire library preparation can be performed with a single clean up step. The entire library preparation can be performed with no more than two clean up steps. The entire library preparation can be performed with only three clean up steps.

In some embodiments, the target-specific primers comprise a 5' randomized tail. In some embodiments, the randomized tail comprises a cleavable 5' end. In some embodiments, the single-stranded polynucleotide is ssDNA. In some embodiments, the single-stranded polynucleotide is RNA. In some embodiments, the primers are random, such as random hexamers. In some embodiments, the primers are a length from 4 to 30 nucleotides in length. In some embodiments, the cleavable 5' end is cleavable by a photocleaving. In some embodiments, the cleavable 5' end is cleavable by a nuclease. In some embodiments, the nuclease is an exonuclease. In some embodiments, the nuclease is an endonuclease. In some embodiments, the nuclease is an RNA nuclease. In some embodiments, the nuclease is a DNA nuclease. In some embodiments, the nuclease is a nuclease that can cleave a DNA-RNA hybrid molecule. In some embodiments, the nuclease is a nuclease that cleaves the RNA component of a DNA-RNA hybrid molecule, such as RNaseH. In some cases, the exonuclease activity is provided by the 5'-3' exonuclease activity of a polymerase, such as DNA Polymerase I. In some cases, the nuclease specifically cleaves dU, such as uracil-DNA glycosylase. In some embodiments, the cleavable 5' end comprises a modification selected from the group consisting of: a fluorophore, a dideoxynucleotide, a deoxynucleotide, a radiolabel, a dye, dUTP, rA, rU, rG, rC, rUTP, and a restriction enzyme target sequence, or any combination thereof. In some embodiments, the cleavable 5' end comprises a dUTP. In some embodiments, the cleavable 5' end comprises a rUTP. In some embodiments, the cleavable 5' end is from 1-5 nucleotides. In some embodiments, the cleavable 5' end is 1 nucleotide. In some embodiments, the cleaving removes between 1-5 nucleotides of the primers. In some embodiments, the cleaving removes one or more nucleotide from the primers. In some embodiments, the cleaving comprises cleaving one or more bases. In some embodiments, the one or more overhangs comprises a thymine. In some embodiments, the one or more overhangs comprises an adenine. In some embodiments, one or more overhangs comprises a guanine. In some embodiments, the one or more overhangs comprises a cytosine. In some embodiments, the one or more overhangs comprises a thymine and the 3' overhang comprises an, adenine. In some embodiments, the one or more overhangs comprises from 1-5 nucleotides. In some embodiments, the one or more overhangs comprises 1-5 nucleotides of a modification selected from the group consisting of: a fluorophore, a dideoxynucleotide, a deoxynucleotide, a radiolabel, a dye, dUTP, rA, rU, rG, rC, rUTP, and a restriction enzyme target sequence, or any combination thereof. In some embodiments, the extending steps (e.g., using dNTP's, dNTP's containing dUTP, rA, rU, rG, rC, rUTP, a fluorophore, a dideoxynucleotide, a deoxynucleotide, a radiolabel, or a dye for downstream purification or degradation) result in a blunt end. In some embodiments, the adapter comprises a sequencing adapter. In some embodiments, the adapter comprises a nucleic acid barcode. In some embodiments, the adapter comprises a nucleic acid barcode sequence. The adapter-ligated library can, in some cases, be sequenced. In some embodiments, the polynucleotide is an ancient polynucleotide. In some embodiments, the polynucleotide comprises less than 10 copies of nucleic acid. In some embodiments, the method is performed two or more times. The entire library preparation can be performed with a single clean up step. The entire library preparation can be performed with no more than two clean up steps. The entire library preparation can be performed with only three clean up steps.

In one aspect the disclosure provides for a method for preparing a library of polynucleotides comprising: contacting a plurality of single stranded polynucleotides with a first set of random primers comprising a cleavable 5' end; extending the primers to generate first extension products hybridized to the polynucleotides thereby forming double-stranded duplexes; cleaving the cleavable 5' end, thereby generating double-stranded duplexes having a first overhang; and ligating one or more adaptors to the double-stranded duplex of the previous step, wherein the one or adaptors comprises an overhang complementary to the first overhangs, and wherein the method comprises only one round of extending. The entire library preparation can be performed with a single clean up step. The entire library preparation can be performed with no more than two clean up steps. The entire library preparation can be performed with only three clean up steps.

In some embodiments, the polynucleotide is ssDNA. In some embodiments, the polynucleotide is RNA. In some embodiments, the printers are random, such as random hexamers. In some embodiments, the primers area length from 4 to 30 nucleotides in length. In some embodiments, the cleavable 5' end is cleavable by photocleaving. In some embodiments, the cleavable 5' end is cleavable by a nuclease. In some embodiments, the nuclease is an exonuclease. In some embodiments, the nuclease is an endonuclease. In some embodiments, the nuclease is an RNA nuclease. In some embodiments, the nuclease is a DNA nuclease. In some embodiments, the nuclease is a nuclease that can cleave a DNA-RNA hybrid molecule. In some embodiments, the nuclease is a nuclease that cleaves the RNA component of a DNA-RNA hybrid molecule, such as RNaseH. In some cases, the exonuclease activity is provided by the 5'-3' exonuclease activity of a polymerase, such as DNA Polymerase I. In some cases, the nuclease specifically cleaves dU, such as uracil-DNA glycosylase. In some embodiments, the cleavable 5' end comprises a modification selected from the group consisting of: a fluorophore, a dideoxynucleotide, a deoxyn In some embodiments, nucleotide, a radiolabel, a dye, dUTP, rA, rU, rG, rC, rUTP, and a restriction enzyme target sequence, or any combination thereof. In some embodiments, the cleavable 5' end comprises a dUTP. In some embodiments, the cleavable 5' end comprises a rUTP. In some embodiments, the cleavable 5' end is from 1-5 nucleotides. In some embodiments, the cleavable 5' end is 1 nucleotide. In some embodiments, the cleaving removes between 1-5 nucleotides of the primers. In some embodiments, the cleaving removes one or more nucleotide from the primers. In some embodiments, the cleaving comprises cleaving one or more bases. In some embodiments, the one or more overhangs comprises a thymine. In some embodiments, the one or more overhangs comprises an adenine. In some embodiments, one or more overhangs comprises a guanine. In some embodiments, the one or more overhangs comprises a cytosine. In some embodiments, the one or more overhangs comprises a thymine and the 3' overhang comprises an adenine. In some embodiments, the one or more overhangs comprises from 1-5 nucleotides. In some embodiments; the one or more overhangs comprises 1-5 nucleotides of a modification selected from the group consisting of: a fluorophore, a dideoxynucleotide, a deoxynucleotide, a radiolabel, a dye, dUTP, rA, rU, rG, rC, rUTP, and a restriction enzyme target sequence, or any combination thereof. In some embodiments, the extending steps (e.g., using dNTP's, dNTP's containing dUTP, rA, rU, rG, rC, rUTP, a fluorophore, a dideoxynucleotide, a deoxynucleotide, a radiolabel, or a dye for downstream purification or degradation) result in a blunt end. In some embodiments, the adapter comprises a sequencing adapter. In some embodiments, the adapter comprises a nucleic acid barcode. In some embodiments, the adapter comprises a nucleic acid randomized barcode that is generated by either adaptor oligonucleotide containing a cleavable 3' or 5' end. In some embodiments, the method further comprises sequencing the adapter-ligated library. In some embodiments, the polynucleotide is an ancient polynucleotide. In some embodiments, the starting single stranded polynucleotides comprises less than 10 copies of a nucleic acid molecule. In some embodiments, the method is performed two or more times. The entire library preparation can be performed with a single clean up, step. The entire library preparation can be performed with no more than two clean up steps. The entire library preparation can be performed with only three clean up steps.

In one aspect the disclosure provides for a method for generating an adaptor-ligated library of double-stranded nucleic acid molecules comprising, in a single reaction vessel or reaction mixture: contacting a plurality of single-stranded polynucleotides with pool of random primers, each comprising a cleavable 5' end; extending the primers to generate first extension products hybridized to the single-stranded polynucleotides, thereby forming first double-stranded duplexes; denaturing the first double-stranded duplexes into single strands; hybridizing the first polynucleotide extension products with primers from a pool of target-specific primers; extending the primers to generate second extension products hybridized to the first extension products, thereby forming second double-stranded duplexes; cleaving the cleavable 5' ends of the first extension products or the second extension products, thereby forming second double-stranded duplexes having one or more overhangs; and ligating one or more double stranded adapters comprising a 3' overhang to the second double-stranded duplexes of the previous stem, thereby forming the adaptor-ligated library wherein the method comprises only two steps of extending. The entire library preparation can be performed with a single clean up step. The entire library preparation can be performed with no more than two clean up steps. The entire library preparation can be performed with only three clean up steps.

In some embodiments, the polynucleotide is DNA. In some embodiments, the polynucleotide is RNA. In some embodiments, the primers are random, such as random hexamers. In some embodiments, the primers are a length from 4 to 30 nucleotides in length. In some embodiments, the cleavable 5' end is cleavable by a photocleaving. In some embodiments, the cleavable 5' end is cleavable by a nuclease. In some embodiments, the nuclease is an exonuclease. In some embodiments, the nuclease is an endonuclease. In some embodiments, the nuclease is an RNA nuclease. In some embodiments, the nuclease is a DNA nuclease. In some embodiments, the nuclease is a nuclease that can cleave a DNA-RNA hybrid molecule. The nuclease can, in some cases, be a nuclease that cleaves the RNA component of a DNA-RNA hybrid molecule, such as RNaseH. In some cases, the exonuclease activity is provided by the 5'-3' exonuclease activity of a polymerase, such as DNA Polymerase I. In some cases, the nuclease specifically cleaves dU, such as uracil-DNA glycosylase. In some embodiments, the cleavable 5' end comprises a modification selected from the group consisting of: a fluorophore, a dideoxynucleotide, a deoxynucleotide, a radiolabel, a dye, dUTP, rA, rU, rG, rC, rUTP, and a restriction enzyme target sequence, or any combination thereof. In some embodiments, the cleavable 5' end comprises a dUTP. In some embodiments, the cleavable 5' end comprises a rUTP. In some embodiments, the cleavable 5' end is from 1-5 nucleotides. In some embodiments, the cleavable 5' end is 1 nucleotide. In some embodiments, the cleaving removes between 1-5 nucleotides of the primers. In some embodiments, the cleaving removes one or more nucleotide from the primers. In some embodiments, the cleaving comprises cleaving one or more bases. In some embodiments, the one or more overhangs comprises a thymine. In some embodiments, the one or more overhangs comprises an adenine. In some embodiments, one or more overhangs comprises a guanine. In some embodiments, the one or more overhangs comprises a cytosine. In some embodiments, the one or more overhangs comprises a thymine and the 3' overhang comprises an adenine. In some embodiments, the one or more overhangs comprises from 1-5 nucleotides. In some embodiments, the one or more overhangs comprises 1-5 nucleotides of a modification selected from the group consisting of: a fluorophore, a dideoxynucleotide, a deoxynucleotide, a radiolabel, a dye, dUTP, rA, rU, rG, rC, rUTP, and a restriction enzyme target sequence, or any combination thereof. In some embodiments, the extending steps (e.g., using dNTP's, dNTP's containing dUTP, rA, rU, rG, rC, rUTP, a fluorophore, a dideoxynucleotide, a deoxynucleotide, a radiolabel, or a dye for downstream purification or degradation) result in a blunt end. In some embodiments, the adapter comprises a sequencing adapter. In some embodiments, the adapter comprises a nucleic acid barcode. In some embodiments, the adapter comprises a nucleic acid barcode. In some embodiments, the adapter comprises a nucleic acid barcode sequence. The adapter-ligated library can, in some cases, be sequenced. In some embodiments, the polynucleotide is an ancient polynucleotide. In some embodiments, the polynucleotide comprises less than 10 copies of nucleic acid. In some embodiments, the method is performed two or more times. The entire library preparation can be performed with a single clean up step. The entire library preparation can be performed with no more than two clean up steps. The entire library preparation can be performed with only three clean up steps.

In one aspect the disclosure provides for a method of generating double-stranded adapters with one or more overhangs. The double-stranded adapters can be generated in a single reaction mixture or reaction vessel. The double-stranded adapters can be generated by annealing two pools of oligonucleotides. Each oligonucleotide within the first pool of oligonucleotides optionally comprises a 5' cleavable nucleotide. Each oligonucleotide within the second pool of oligonucleotides can comprise a sequence that is complementary to a portion of an oligonucleotide in the first pool and a 5' cleavable nucleotide. In some cases, each oligonucleotide from the second pool of oligonucleotides can comprise a barcode sequence between the sequence that is complementary to a portion of an oligonucleotide in the first pool and the 5' cleavable nucleotide. The barcode sequences can be random. The barcode sequences can be non-random. The barcode sequences can be semi-random, such as, for example, oligonucleotides prepared by the use of semi-degenerate primer synthesis. The oligonucleotides from the first pool can be hybridize to oligonucleotides from the second pool to form a duplex. The oligonucleotide from the first pool in the duplex can be extended, thereby covalently attaching the oligonucleotide from the first pool to a sequence that is complementary to the optional barcode sequence and complementary to the cleavable nucleotide(s) of the oligonucleotide from the second pool. The one or more cleavable nucleotides at one or more ends the adapters can be cleaved. The cleaved adapters can be used in any of the methods herein for library preparation and sequencing. In some cases, the second pool of oligonucleotides comprises more than three or more, four or more, five or more, six or more, seven or more, eight or more, ten or more, 12 or more, 14 or more, 16 or more, 18 or more, 20 or more, 22 or more, 24 or more, 26 or more, 28 or more, 30 or more, 32 or more, 36 or more, 42 or more, 48 or more, 54 or more, 60 or more, 64 or more, 66 or more, 72 or more, 78 or more, 84 or more, 90 or more, 98 or more, 120 more, 128 or more, 160 or more, 200 or more, 240 or more, 256 or more, 280 or more, 512 or more, 1024 or more, 2048 or more, or 4096 or more different sequence barcodes.

The oligonucleotides can be from 4 to 150 nucleotides in length. The oligonucleotides can be completely complementary except for the random barcodes and 5' cleavable nucleotides. In some embodiments, the oligonucleotides are only partially complementary. In some examples, the cleavable 5' end is cleavable by a photocleaving. In some embodiments, the cleavable 5' end is cleavable by a nuclease. In some embodiments, the nuclease is an exonuclease. In some embodiments, the nuclease is an endonuclease. In some embodiments, the nuclease is an RNA nuclease. In some embodiments, the nuclease is a DNA nuclease. In some embodiments, the nuclease is a nuclease that can cleave, a DNA-RNA hybrid molecule. In some embodiments, the nuclease is a nuclease that cleaves the RNA component of a DNA-RNA hybrid molecule, such as RNaseH. In some cases, the exonuclease activity is provided by the 5'-3' exonuclease activity of a polymerase, such as DNA Polymerase I. In some cases, the nuclease specifically cleaves dU, such as uracil-DNA glycosylase. In some embodiments, the cleavable 5' end comprises a modification selected from the group consisting of: a fluorophore, a dideoxynudeotide, a deoxynucleotide, a radiolabel, a dye, dUTP, rA, rU, rG, rC, rUTP, and a restriction enzyme target sequence, or any combination thereof. In some embodiments, the cleavable 5' end comprises a dUTP. In some embodiments, the cleavable 5' end comprises a rUTP. In some embodiments, the cleavable 5' end is from 1-5 nucleotides. In some embodiments, the cleavable 5' end is 1 nucleotide. In some embodiments, the cleaving removes between 1-5 nucleotides of the primers. In some embodiments, the cleaving removes one or more nucleotide from the primers. In some embodiments, the cleaving comprises cleaving one or more bases. In some embodiments, the one or more overhangs comprises a thymine. In some embodiments, the one or more overhangs comprises an adenine. In some embodiments, one or more overhangs comprises a guanine. In some embodiments, the one or more overhangs comprises a cytosine. In some embodiments, the adapter comprises a nucleic acid randomized barcode that is generated by either adaptor oligonucleotide containing a cleavable 3' or 5' end. In some embodiments, the method further comprises sequencing the adapter-ligated library.

In one aspect the disclosure provides for a kit comprising: a first container comprising a set of random primers, each comprising a cleavable 5' end; a second container comprising a polymerase; a third container comprising adaptors, wherein each of the adaptors comprises an overhang complementary to the cleavable 5' end; and instructions for use, wherein the instructions indicate use of the random primers for only two rounds of extension. In some embodiments, the kit further comprises a container comprising a ligase. In some embodiments, the kit further comprises a container comprising a buffer.

In particular examples of generating double-stranded nucleic acid fragments with overhangs or double-stranded adapters with overhangs, the 5' cleavable end comprises one or more RNA bases or one or more dU. If the 5' cleavable end comprises an RNA base, the cleaving can in some cases be mediated by RNaseH or the 5'→3' exonuclease activity of a polymerase, such as DNA Polymerase I. If the cleavable 5' end comprises dU, the cleaving can be mediate by uracil-DNA glycosylase. Upon cleavage of the 5' cleavable end, the double-stranded nucleic acid fragment or double-stranded adapter can have one or more overhangs. These overhangs can improve the efficiency of ligation reactions to sequences with complementary overhangs. The nucleic acid fragments with 3' overhangs can then be ligated to adapters with complementary 3' overhangs to generate adapter-ligated sequencing libraries.

In one aspect the disclosure provides for a kit comprising: a first container comprising a set of random primers, each comprising a cleavable 5' end; a second container comprising a polymerase; a third container comprising adaptors, wherein each of the adaptors comprises overhangs complementary to the cleavable 5' end; and instructions for use, wherein the instructions indicate use of the pool of random primers for only one round of extension. In some embodiments, the kit further comprises a container comprising a ligase. In some embodiments, the kit further comprises a container comprising a buffer.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION

Definitions

Figure 1A:
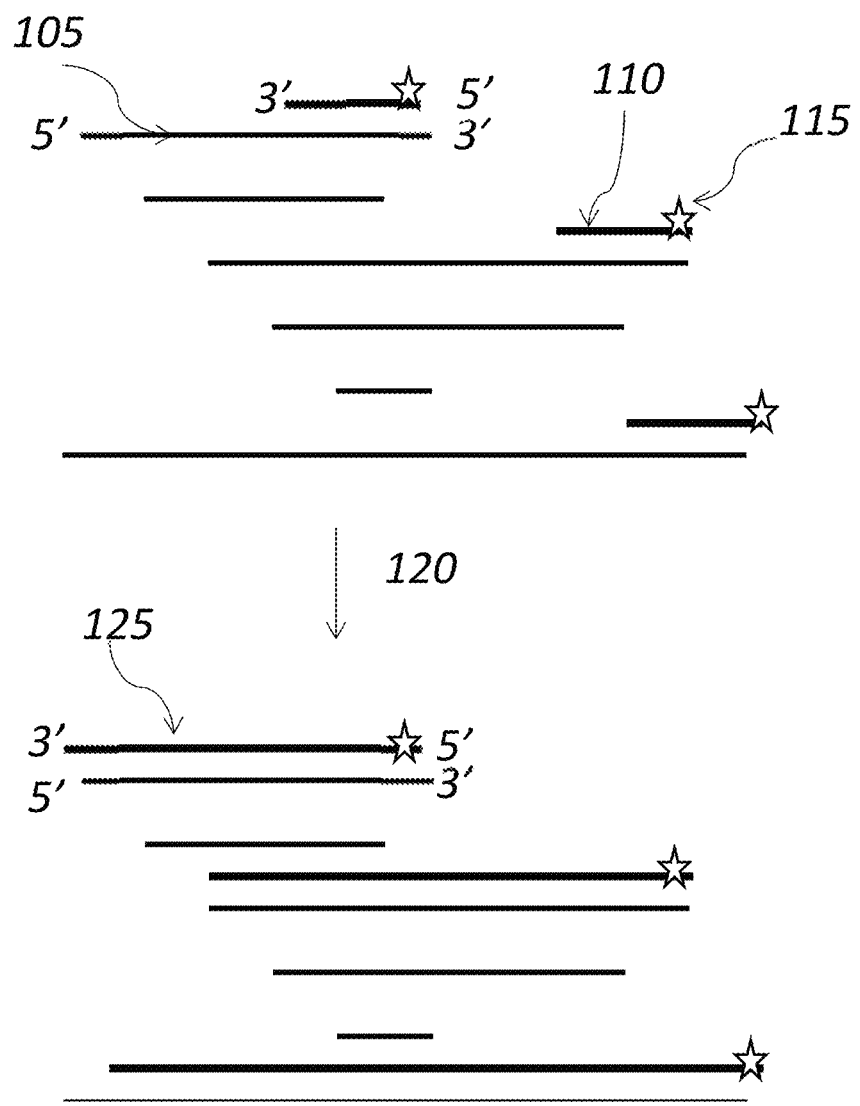
FIGS. 1A-C depict an exemplary embodiment of a double amplification method of the disclosure.

As used herein, "cleavable end" can refer to a nucleotide at or near the 3' or 5' end of a nucleic acid that is cleavable. The cleavable end can be cleaved by non-enzymatic or enzymatic means including chemical, thermal, or photolytic, to enable release of the cleavable end. A cleavable end may refer both to the selectively cleavable functional group and also to protected forms thereof. The cleavable end may, for example, be located along the polymer backbone (i.e., a modified 3'-5' internucleotide linkage in place of one of the phosphodiester groups), as a substituent on or replacement of one of the bases or sugars of the oligonucleotide primer, and/or as the 3' terminal residue (e.g., a ribonucleotide at the 3' end of the oligodeoxyribonucleotide primer). The cleavable end can be stable under standard solid phase DNA synthesis conditions, during primer immobilization, hybridization, primer extension, and washing conditions. A cleavable end may also comprise a nucleotide cleavable by an enzyme such as a nuclease. For example, the cleavable end may be a restriction endonuclease site. Exemplary restriction endonucleases for use in cleaving at the cleavable end can include BpmI, BsgI, BseRI, BsmFI, and FokI.

A cleavable end may also be a nucleotide or series of nucleotides capable of blocking or terminating 5' to 3' enzyme-promoted digestion by an enzyme having 5' to 3' exonuclease activity, such as T7 gene 6 exonuclease. Representative blocking nucleotides can be those comprising a phosphorothioate, borano-phosphate, or peptide group. The blocking nucleotide and/or cleavable end can be one which does not inhibit enzymatic extension of the primer.

As used here, the term "adaptor" or "adapter" are used interchangeably and can refer to an oligonucleotide that may be attached to the end of a nucleic acid. Adaptor sequences may comprise, for example, priming sites, the complement of a priming site, recognition sites for endonucleases, common sequences and promoters. Adaptors may also incorporate modified nucleotides that modify the properties of the adaptor sequence. For example, phosphorothioate groups may be incorporated in one of the adaptor strands.

The term "pool" or "set" as used herein can be used interchangeably and can refer to a collection of molecules. The molecules in the set can be identical or different from each other.

The term "complementary" as used herein can refer to the hybridization or base pairing between nucleotides or nucleic acids, such as, for instance, between the two strands of a double stranded DNA molecule or between an oligonucleotide primer and a primer binding site on a single stranded nucleic acid to be sequenced or amplified. Complementary nucleotides can be, generally, A (adenine) and T (thymine) (or A and U), or C (cytosine) and G (guanine). Two single stranded RNA or DNA molecules can be complementary when the nucleotides of one strand, optimally aligned and compared and with appropriate nucleotide insertions or deletions, pair to the nucleotides of the other strand. Complementarity can exist when an RNA or DNA strand hybridizes under selective hybridization conditions to its complement.

The term "primer" as used herein can refer to a single-stranded oligonucleotide capable of acting as a point of initiation for template-directed DNA synthesis under suitable conditions for example, buffer and temperature, in the presence of four different nucleoside triphosphates and an agent for polymerization, such as, for example, DNA or RNA polymerase or reverse transcriptase. A primer can be sufficiently complementary to hybridize with such template. A primer can comprise a primer site which can refer to the area of the primer which hybridizes to a target nucleic acid. The primer can be a primer in a pool of primers. The primer can be part of a primer pair. A primer pair (e.g., target-specific primer) can include a 5' upstream primer that hybridizes with the 5' end of the sequence to be amplified and a 3' downstream primer that hybridizes with the complement of the 3' end of the sequence to be amplified.

General Overview

Figure 1B:
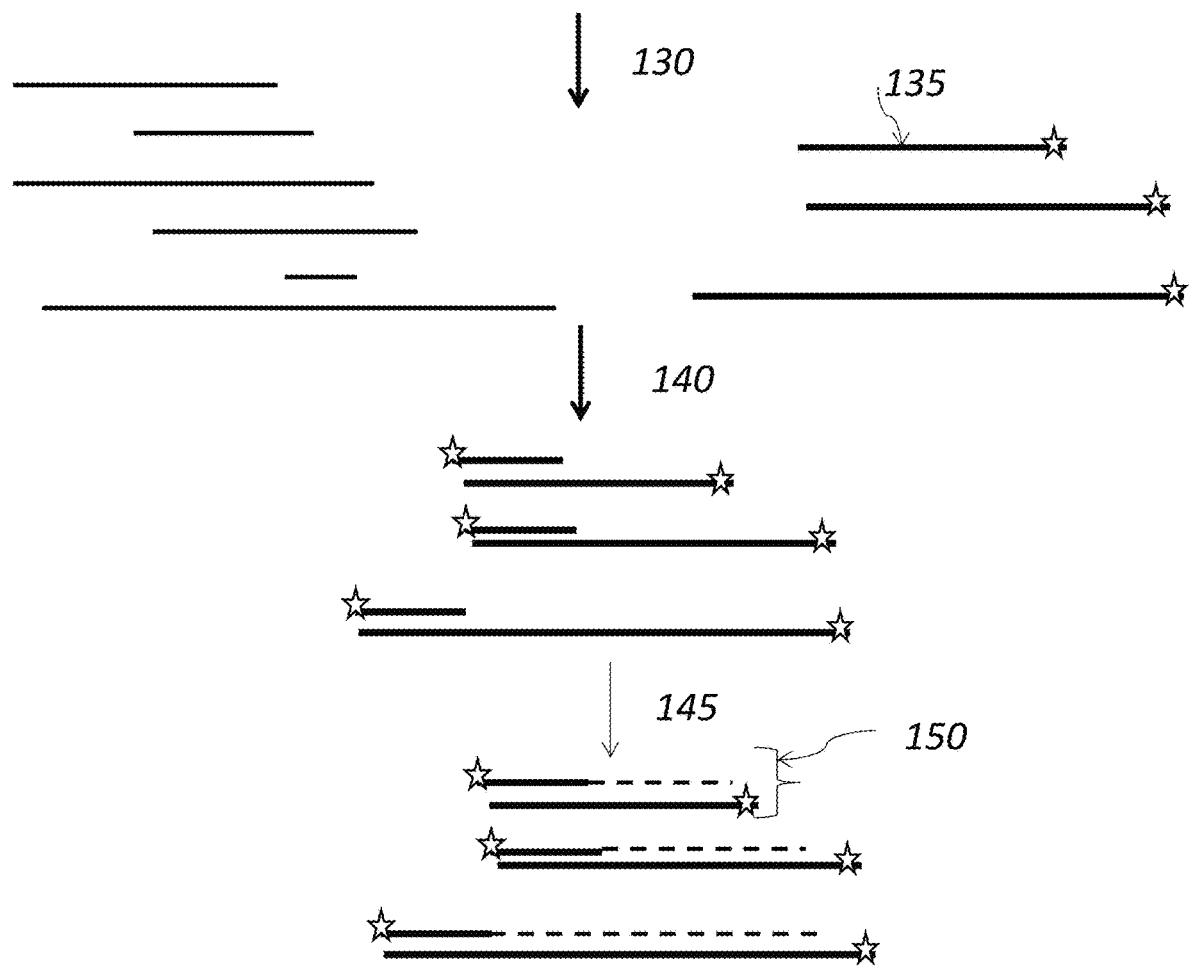
Figure 1C:
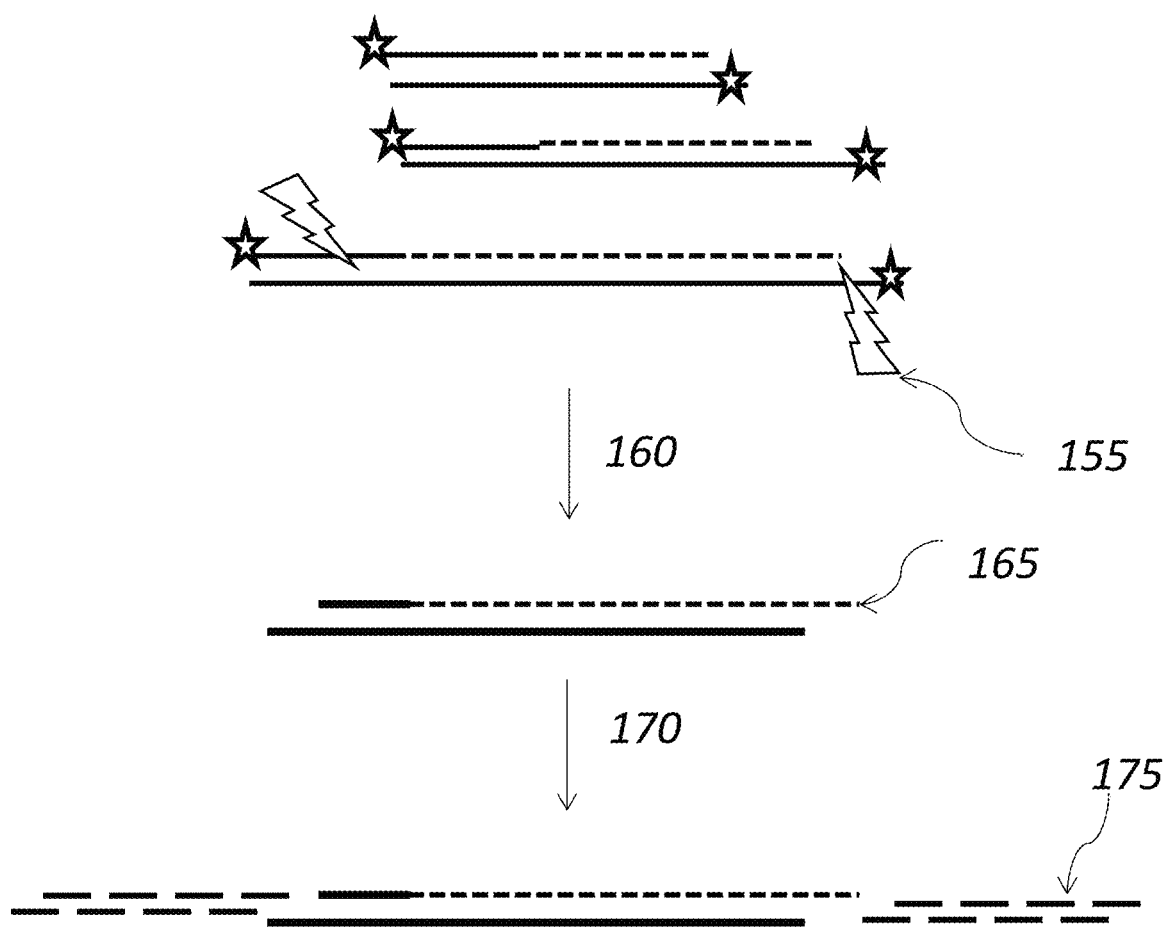

In some embodiments, the disclosure provides for a method of ligating one or more adapters to a double-stranded nucleic acid. FIGS. 1A-1C depict an exemplary embodiment of the methods of the disclosure. A single-stranded nucleic acid 105 can be contacted with a primer or a pool of random primers 110. The primer(s) can comprise a cleavable 5' end 115. The primer can be extended 120 to form first double-stranded duplex(es) 125. The first double-stranded duplex(es) 125 can be denatured 130 into single-strands 135 of the first double-stranded duplex(es) 125. The same (or different) primer(s) used in the first contacting step can be then contacted 140 to the denatured single-strands 135. The primer can be extended 145 to generate a second double-stranded duplex(es) 150. One or more 5' cleavable ends of the second double-stranded duplex(es) 150 can contacted with a cleavage agent 155, which can cleave 160 the one or more 5' cleavable ends thereby generating one or more overhangs 165. The one or more overhangs 165 can be ligated 170 to a double-stranded nucleic acid 175 (e.g., a sequencing adapter) that comprises overhangs complementary to the one or more overhangs of the second double-stranded duplex 150. All of the above steps are preferably performed in a single reaction vessel or reaction mixture. The method described can be performed with a single clean up step prior to ligation. The entire library preparation can be performed with a single clean up step. The entire library preparation can be performed with no more than two clean up steps. The entire library preparation can be performed with only three clean up steps. Clean up can refer to methods of separating target nucleic acid molecules from impurities, buffers, or undesired nucleic acid molecules, such as unligated adapters. Clean up methods can comprise columns, such as Qiagen DNA columns or Qiagen MinElute reaction clean up kit, or bead-based methods, such as Ampure XP beads.

Figure 2A:
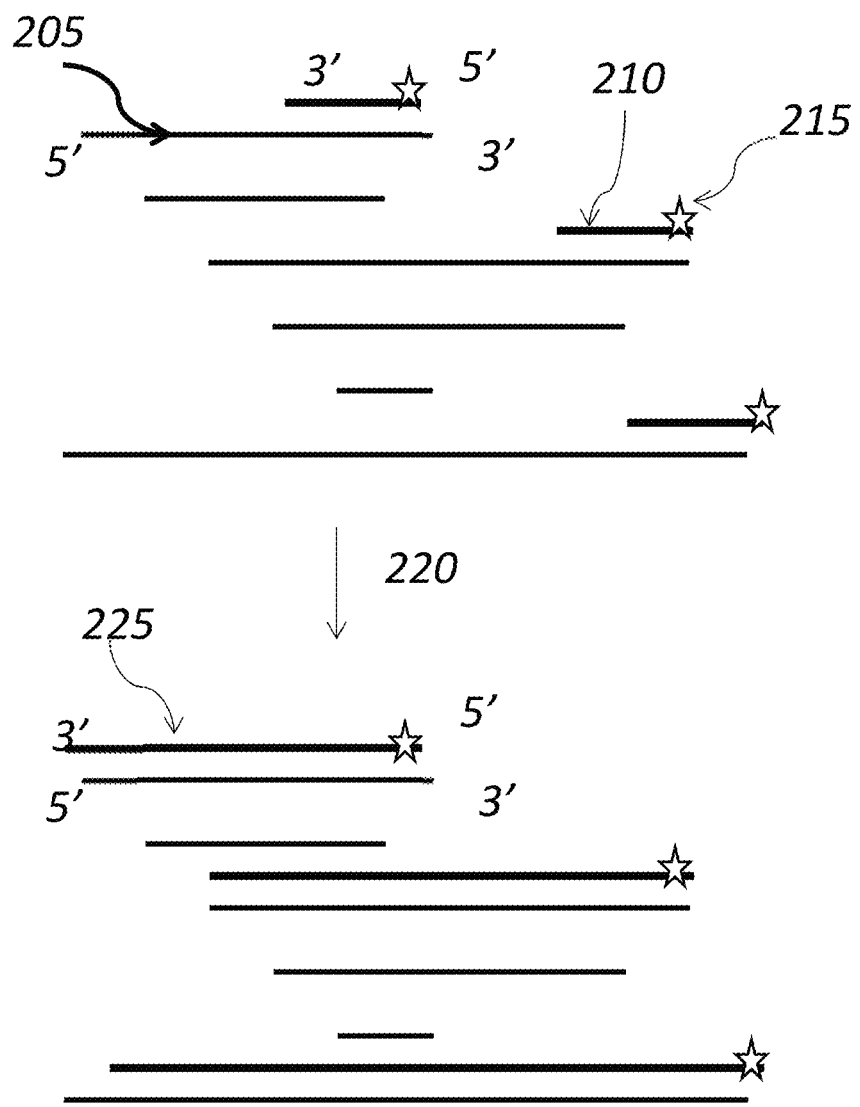
FIGS. 2A-B depict an exemplary embodiment of a single amplification method of the disclosure.
Figure 2B:
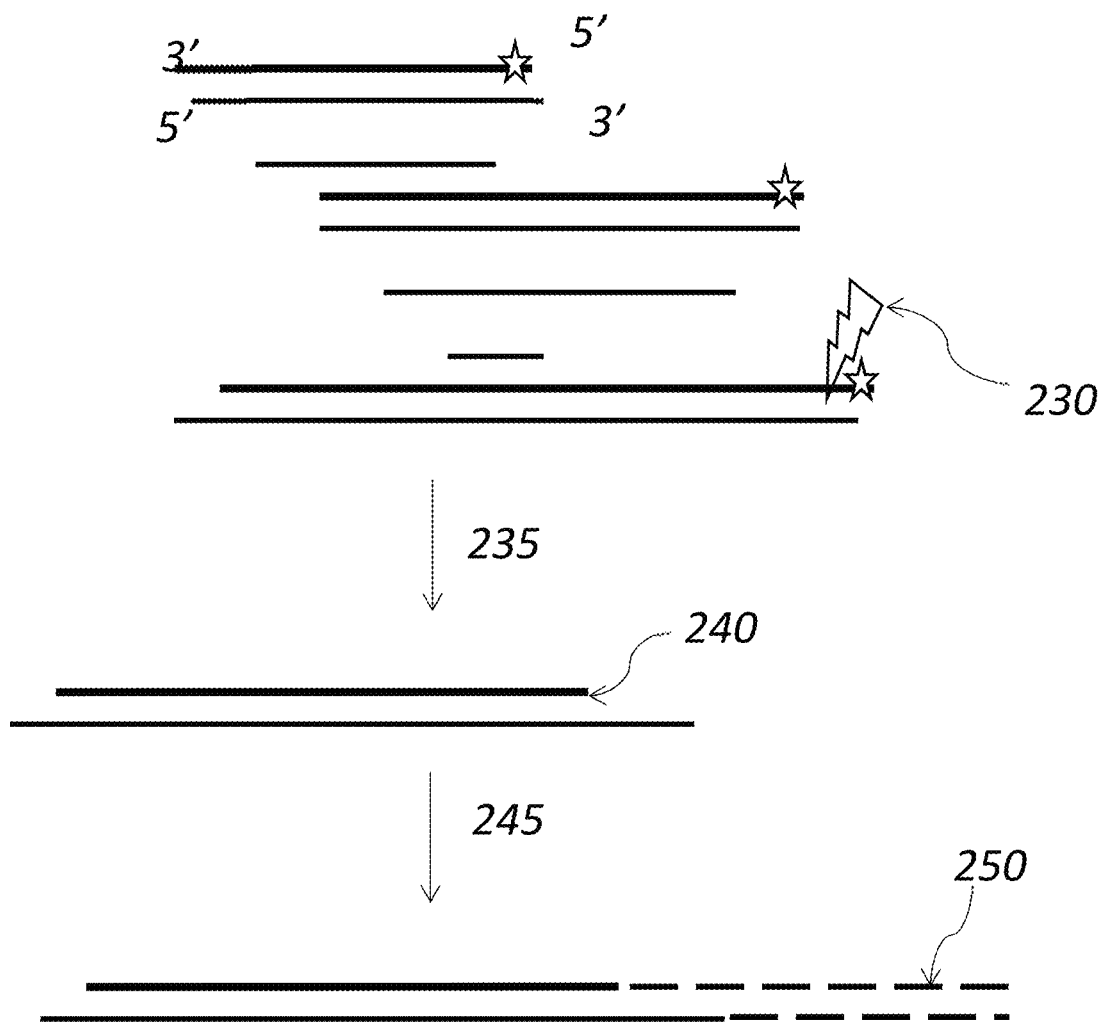

In some embodiments, the methods of the disclosure provide for a method of ligating one or more adapters to a double-stranded nucleic acid, wherein the method only uses one round of extension (e.g., amplification). FIGS. 2A-2B depict an exemplary embodiment of the methods of the disclosure wherein only one round of extension is used. A single-stranded nucleic acid 205 can be contacted with a primer (e.g., a primer of a pool of random primers) 210. The primer can comprise a cleavable 5' end 215. The primer can be extended 220 to form a first double-stranded duplex 225. One or more 5' cleavable ends of the second double-stranded duplex 225 can contacted with a cleavage agent 230, which can cleave 235 the one or more 5' cleavable ends thereby generating one or more overhangs 240. The one or more overhangs 240 can be ligated 245 to a double-stranded nucleic acid 250 (e.g., a sequencing adapter) that comprises overhangs complementary to the one or more overhangs of the first double-stranded duplex 225.

Primers

The disclosure provides for primers comprising one or more modifications (e.g., cleavable nucleotides). The one or more modifications (e.g., cleavable nucleotides) can be at the 5' end. The one or more modifications (e.g., cleavable nucleotides) can be at the 3' end. The one or more modifications (e.g., cleavable nucleotides) can be between the ends of the primer. In some instances, the one or more modifications (e.g., cleavable nucleotides) are at the 5'end.

The one or more cleavable nucleotides can comprise at least 1, 2, 3, 4, 5, 6, 7, 8, 9, or 10 or more nucleotides. The one or more cleavable nucleotides can comprise at most 1, 2, 3, 4, 5, 6, 7, 8, 9, or 10 or more nucleotides. Exemplary cleavable nucleotides can include RNA, DNA, PNA, or LNA, dU, dA, dT, dC, and dG, or any combination thereof. In some embodiments, the cleavable nucleotides are RNA nucleotides.

The cleavable nucleotides can comprise a modification. A non-cleavable nucleotide can comprise a modification that enables it to be cleavable. Exemplary modifications can include, but are not limited to, biotinylated nucleotides, methylated nucleotides, acetylated nucleotides, PNA nucleotides, polyadenylation, polyuridylation, and LNA nucleotides. In some instances, an exemplary modification is a 5' 7-methylguanosine that can be added by a guanylyltransferase.

The primer can be at least 1, 2, 3, 4, 5, 6, 7, 8, 9, or 10 or more nucleotides in length. The primer can be at most 1, 2, 3, 4, 5, 6, 7, 8, 9, or 10 or more nucleotides in length. In some instances, the primer is 6 nucleotides in length (hexamer).

The primer can be part of a pool of primers. The pool of primers can comprise at least 100, 500, 1000, 1500, 2000, 2500, 3000, 3500; 4000, 4500, or 5000 or more primers. The pool of primers can comprise at most 100, 500, 1000, 1500, 2000, 2500, 3000, 3500, 4000, 4500, or 5000 or more primers.

The primer can be a random primer (e.g., a random hexamer primer). A pool of random primers can comprise primers that are substantially different from one another. A pool of random primers can hybridize to a plurality of locations within a target nucleic acid. A pool of random primers can have primers wherein each primer is different from every other primer. A primer in a pool of random primers can have at least 1, 2, 3, 4, 5, 6, 7, 8, 9, or 10% or more complementarity and/or identity to another primer in the pool of random primers. A primer in a pool of random primers can have at most 1, 2, 3, 4, 5, 6, 7, 8, 9, or 10% or more complementarity and/or identity to another primer in the pool of random primers.

The primer can be a target-specific primer. A target specific primer can be a primer that is designed to hybridize to a specific region of a target nucleic acid. A target-specific primer can hybridize to a target nucleic acid with at least 30, 40, 50, 60, 70, 80, 90, 95, or 100% complementarity. A target-specific primer can hybridize to a target nucleic acid with at most 30, 40, 50, 60, 70, 80, 90, 95, or 100% complementarity. A target-specific primer can hybridize to a target nucleic acid over at least 10, 20, 30, 40, 50, 60, 70, 80, 90, or 100% of the length of the primer. A target-specific primer can hybridize to a target nucleic acid over at most 10, 20, 30, 40, 50, 60, 70, 80, 90, or 100% of the length of the primer. A target-specific primer can hybridize to a target nucleic acid with at least 1, 2, 3, 4, 5, 6, 7, 8, 9, or 10 or more mismatches. A target-specific primer can hybridize to a target nucleic acid with at most 1, 2, 3, 4, 5, 6, 7, 8, 9, or 10 or more mismatches.

In some instances, a target-specific primer comprises a tail. A tail can be at least 1, 2, 3, 4, 5, 6, 7, 8, 9, 10 or more nucleotides in length. A tail can be at most 1, 2, 3, 4, 5, 6, 7, 8, 9, or 10 or more nucleotides in length. A tail can be from 1-5 nucleotides, from 1-10 nucleotides, from 1-15 nucleotides, from 1-30 nucleotides, from 5-10 nucleotides, from 5-15 nucleotides, or from 5-30 nucleotides in length. A tail can comprise a random sequence. A tail can comprise a random hexamer. A tail comprising a random sequence can be any random sequence of the disclosure. For example, a random tail sequence can comprise a nucleotide, such as, for example, a fluorophore, a dideoxynucleotide, a deoxynucleotide, a radiolabel, a dye, dUTP, rA, rU, rG, rC, rUTP, a 5'7-methylguanosine added by a guanylyltransferase, or a restriction enzyme target sequence.

Methods

The disclosure provides for methods for sample preparation (e.g., adaptor ligation for sequencing). A sample comprising single-stranded nucleic acid (e.g., RNA and/or DNA) can be contacted with a primer of the disclosure. The primer can comprise a modification (e.g., a cleavable nucleotide at its 5' end). The primer (or primers in a pool of primers) can bind to one or more locations within the pool of target nucleic acids (e.g., fragmented target nucleic acids). The primer (or primers in a pool of primers) can bind to a specific location within the pool of target nucleic acids.

The primer can be extended (e.g., using dNTP's, dNTP's containing dUTP, rA, rU, rG, rC, rUTP, a fluorophore, a dideoxynucleotide, a deoxynucleotide; a radiolabel, or a dye for downstream purification or degradation). In some instances, primer extension occurs only one time. The length of primer extension can be dependent on the type of polymerase used to perform the extension. Exemplary polymerases that may be used for extension can include, but are not limited to, DNA polymerases, RNA polymerases, reverse transcriptases, DNA polymerase I, polyA polymerase, Bst Polymerase Large Fragment, Bst 2.0 (NEB), Bst 2.0 Warmstart polymerase, Klenow (exo-), Klenow Large Fragment, DNA Polymerase I Large (Klenow) Fragment, T4 DNA polymerase, Bsu Polymerase Large Fragment, Sulfolobus DNA polymerase, Deep Vent (exo-) DNA Polymerase (NEB), Deep Vent DNA Polymerase (NEB), Vent DNA Polymerase, Taq, phi29, T7 RNA polymerase, transferases (e.g., .g.guanylyl transferase to add 5' 7-methylguanosine, methyltransferases, acyltransferases, selenotransferases, transketolases, glycosyltransferases, acyltransferases) and rTth DNA polymerase. The length of the primer extension product can be at least 100, 200, 300, 400, 500, 600, 700, 800, 900, 1000, 1100, 1200, 1300, 1400, 1500, 1600, 1700, 1800, 1900 or 2000 or more bases. The length of the primer extension product can be at most 100, 200, 300, 400, 500, 600, 700, 800, 900, 1000, 1100, 1200, 1300, 1400, 1500, 1600, 1700, 1800, 1900 or 2000 or more bases. Primer extension can create a double-stranded duplex wherein one strand comprises a cleavable 5' end. Extension can occur at room-temperature. Extension can occur without varying the temperature of the reaction.

In some instances, the method comprises a second round of extension. A second round of extension comprises denaturing the double-stranded duplex comprising a cleavable 5' end into its respective single strands. One strand of the denatured double-stranded duplex can correspond to the original single-stranded target nucleic acid. One strand of the denatured double-stranded duplex can correspond to the primer extension product incorporating the cleavable 5' end. In the second round of extension, primers from the pool of primers can hybridize to one or more regions on the primer extension product. The primers can be extended through primer extension. The length of primer extension can be dependent on the type of polymerase used to perform the extension. Exemplary polymerases that may be used for extension can include, but are not limited to, DNA polymerases, RNA polymerases, reverse transcriptases, DNA polymerase I, polyA polymerase, Bst Polymerase Large Fragment, Bst 2.0 (NEB), Bst 2.0 Warmstart polymerase, Klenow (exo-), Klenow Large Fragment, DNA Polymerase I Large (Klenow) Fragment, T4 DNA polymerase, Bsu Polymerase Large Fragment, Sulfolobus DNA polymerase, Deep Vent (exo-) DNA Polymerase (NEB), Deep Vent DNA Polymerase (NEB), Vent DNA Polymerase, Taq, phi29, T7 RNA polymerase, transferases (e.g., .g.guanylyl transferase to add 5' 7-methylguanosine, methyltransferases, acyltransferases, selenotransferases, transketolases, glycosyltransferases, acyltransferases) and rTth DNA polymerase. The length of the second primer extension product can be at least 100, 200, 300, 400, 500, 600, 700, 800, 900, 1000, 1100, 1200, 1300, 1400, 1500, 1600, 1700, 1800, 1900 or 2000 or more bases. The length of the second primer extension product can be at most 100, 200, 300, 400, 500, 600, 700, 800, 900, 1000, 1100, 1200, 1300, 1400, 1500, 1600, 1700, 1800, 1900 or 2000 or more bases. Primer extension can create a double-stranded duplex wherein both strands comprise a cleavable 5' end.

When there are two rounds of primer extension the first round of extension can be performed with a target-specific primer and the second round can be performed with a random primer. When there are two rounds of primer extension the first round of extension can be performed with a random primer and the second round can be performed with a target-specific primer.

In some instances there can be multiple rounds of primer extension. The number of rounds of primer extension can be at least 1, 2, 3, 4, 5, 6, 7, 8, 9, or 10 or more. The number of rounds of primer extension can be at most 1, 2, 3, 4, 5, 6, 7, 8, 9, or 10 or more. In some instances, one round of primer extension is performed. In some instances, two rounds of primer extension are performed.

Ligation of Adaptors

The double-stranded duplex comprising one or two cleavable ends can be cleaved with a cleavage agent to remove the cleavable end. The cleavage agent can be specific for the cleavable nucleotide on the 5' cleavable end. For example, if the nucleotide is uracil, the cleavage agent may be uracil-DNA glycosylase (UDG). Exemplary uracil-DNA glycosylases can include, but are not limited to, E. coli uracil-DNA glycosylase (NEB), uracil DNA-glycosylase (Life Technologies), Afu Uracil-DNA Glycosylase, Antartic Thermolabile uracil DNA-glycosylase, Epicentre HK-Uracil-N-Glycosylase, Thermolabile Uracil-N-Glycosylase, or Uracil-DNA Excision Mix, or ThermoScientific Uracil-DNA Glycosylase. The cleavage agent can be non-specific for a particular sequence. For example, the cleavage agent can be a prokaryotic DNA Polymerase I that maintains its 5'→3' exonuclease activity. DNA Polymerase I can be from different organisms (e.g. E. coli, B. subtilis, and Thermus aquaticus). Such DNA Polymerase I can be purchased, for example, from New England BioLabs, Life Technologies, and Epicentre. In other examples, the cleavage agent can be a nuclease that cleaves the RNA portion of a DNA-RNA hybrid molecule. Such nucleases can include, but are not limited to, RNaseHybridase Thermostable RNAse H (Epicentre), RBase HII, RNase If, RNAse A, Rnase I, Rnase P, RNase T1, and Riboshredder Rnase Blend. The cleavage agent can cleave the phosphodiester bond between the cleavable nucleotide and an adjacent non-cleavable nucleotide. The cleavage agent can cleave off at least 1, 2, 3, 4, 5, 6, 7, 8, 9, or 10 or more nucleotides of the one or more 5' cleavable ends. The cleavage agent can cleave off at most 1, 2, 3, 4, 5, 6, 7, 8, 9, or 10 or more nucleotides of the one or more 5' cleavable ends. In a particularly preferred embodiment, the cleaving creates overhangs with identical sequences, which allows the ligation of adapters with the complementary overhang.

The cleavage agent can be a nuclease. A nuclease can be an endonuclease. Examples of endonucleases include restriction enzymes, type I endonucleases, type II endonucleases, T7 endonuclease, T4 endonuclease, Bal 31 endonuclease SI nuclease, AP endonuclease, DNaseI, and Endo R. A nuclease can be an exonuclease. Examples of exonucleases include 5'-3' exonucleases, 3'-5' exonucleases, exonuclease I, exonuclease II, exonuclease III, exonuclease IV, exonuclease V, T7 exonuclease, and lambda exonuclease. A nuclease can be a DNA nuclease. A nuclease can be an RNA nuclease. Examples of RNA nucleases can include RNaseA, RNaseH, and RNase T1. A nuclease can cleave a DNA. A nuclease can cleave a RNA. A nuclease can cleave one or more strands of an RNA-DNA hybrid.

Cleavage of the 5' cleavable ends can result in overhangs. The overhangs can be at least 1, 2, 3, 4, 5, 6, 7, 8, 9, or 10 or more nucleotides in length. The overhangs can be at most 1, 2, 3, 4, 5, 6, 7, 8, 9, or 10 or more nucleotides in length. The overhangs can be from 1-5 nucleotides, from 1-10 nucleotides, from 1-15 nucleotides, from 1-30 nucleotides, from 5-10 nucleotides, from 5-15 nucleotides, or from 5-30 nucleotides. The overhangs can comprise one or more nucleotides with a modification. Exemplary modifications can include, for example, a fluorophore, a dideoxynucleotide, a deoxynucleotide, a radiolabel, a dye, dUTP, rA, rU, rG, rC, rUTP, and a restriction enzyme target sequence.

In some instances, the overhangs are one nucleotide in length. The one nucleotide overhang can be an A, T, G, C, or U. In some instances, the one nucleotide overhang is an A. In some instances, the one nucleotide overhang is a T.

The adaptors to be ligated can comprise overhangs. The overhangs of the adaptors can be complementary to the overhangs of the cleavable ends (i.e., the overhangs of the adaptors can hybridize to the overhangs of the cleavable ends by forming sticky ends).

Adaptors to be ligated can comprise a sequencing adaptor (e.g., for deep sequencing). Adaptors to be ligated can comprise a nucleic acid barcode sequence (e.g., for tagging nucleic acid samples). Adapters can comprise a nucleic acid randomized barcode that is generated by either adaptor oligonucleotide containing a cleavable 3' or 5' end. Adaptors can comprise any nucleic acid sequence (e.g., restriction enzyme sequence, modified nucleotides, cleavable nucleotides, non-cleavable nucleotides). The adaptor may be entirely or substantially double stranded. The adaptor may comprise a secondary structure. A double stranded adaptor may comprise two oligonucleotides that are at least partially complementary. The adaptor may be phosphorylated or unphosphorylated on one or both strands. The adaptor may comprise a double stranded section and a single stranded overhang section that is completely or partially complementary to an overhang. For example, when DNA is digested with the restriction enzyme EcoRI the resulting double stranded fragments can be flanked at either end by the single stranded overhang 5'-AATT-3', an adaptor that carries a single stranded overhang 5'-AATT-3' can hybridize to the fragment through complementarity between the overhanging regions. This "sticky end" hybridization of the adaptor to the fragment can facilitate ligation of the adaptor to the fragment. Blunt ended ligation can also be possible. Blunt ends can be converted to sticky ends using the exonuclease activity of the Klenow fragment. For example when DNA is digested with PvuII the blunt ends can be converted to a two base pair overhang by incubating the fragments with Klenow in the presence of dTTP and dCTP. Overhangs may also be converted to blunt ends by filling in an overhang or removing an overhang.

Ligation can occur through the use of a ligase. Exemplary ligases can include Ampligase Thermostable DNA Ligase, E. coli DNA Ligase, Taq DNA Ligase, T7 DNA Ligase, T3 DNA Ligase, 9° N DNA Ligase, ElectroLigase (NEB), DNA ligases, RNA ligases, T4 DNA ligase, DNA ligase I, DNA ligase III, and DNA ligase IV. Methods of ligation can include using T4 DNA Ligase, which catalyzes the formation of a phosphodiester bond between juxtaposed 5' phosphate and 3' hydroxyl termini in duplex DNA or RNA with blunt and sticky ends; Taq DNA Ligase which catalyzes the formation of a phosphodiester bond between juxtaposed 5' phosphate and 3' hydroxyl termini of two adjacent oligonucleotides which are hybridized to a complementary target DNA; E. coli DNA ligase which catalyzes the formation of a phosphodiester bond between juxtaposed 5'-phosphate and 3'-hydroxyl termini in duplex DNA containing cohesive ends; and T4 RNA ligase which catalyzes ligation of a 5' phosphoryl-terminated nucleic acid donor to a 3' hydroxyl-terminated nucleic acid acceptor through the formation of a 3' to 5' phosphodiester bond. The efficiency of the ligation of any of the disclosed methods of ligating adapters to nucleic acids with with overhangs generated by cleaving a cleavable 5' nucleotide can be >50%, >60%, >70%, >80%, >90%, >95%, >98%, >99%, or >99.5%.

In some embodiments a double stranded adaptor is used and only one strand is ligated to the primer extension products. Ligation of one strand of an adaptor may be selectively blocked. For example, one strand of the adaptor can be designed to introduce a gap of one or more nucleotides between the 5' end of that strand of the adaptor and the 3' end of the target nucleic acid. Absence of a phosphate from the 5' end of an adaptor can block ligation of that 5' end to an available 3'OH.

Sequencing

The double-stranded product comprising the single-stranded polynucleotide ligated to the adaptor can be sequenced. Exemplary sequencing techniques can include, for example emulsion PCR (pyrosequencing from Roche 454, semiconductor sequencing from Ion Torrent, SOLiD sequencing by ligation from Life Technologies, sequencing by synthesis from Intelligent Biosystems), bridge amplification on the flow cell (e.g. Solexa/Illumina), isothermal amplification by Wildfire technology (Life Technologies) or rolonies/nanoballs generated by rolling circle amplification (Complete Genomics, Intelligent Biosystems, Polonator). Sequencing technologies like Heliscope (Helicos), SMRT technology (Pacific Biosciences) or nanopore sequencing (Oxford Nanopore) allow direct sequencing of single molecules without prior clonal amplification may be suitable sequencing platforms.

Samples

Samples used in the methods of the disclosure can include a variety of sources and compositions that contain nucleic acids. The sample may be a biological sample but the term also includes other, e.g. artificial samples which comprise nucleic acids such as e.g. PCR products or compositions comprising already purified nucleic acids. Exemplary samples can include, but are not limited to, whole blood; blood products; red blood cells; white blood cells; buffy coat; swabs; urine; sputum; saliva; semen; lymphatic fluid; amniotic fluid; cerebrospinal fluid; peritoneal effusions; pleural effusions; biopsy samples; fluid from cysts; synovial fluid; vitreous humor; aqueous humor; bursa fluid; eye washes; eye aspirates; plasma; serum; pulmonary lavage; lung aspirates; animal, including human or plant tissues, including but not limited to, liver, spleen, kidney, lung, intestine, brain, heart, muscle, pancreas, cell cultures, as well as lysates, extracts, or materials and fractions obtained from the samples described above or any cells and microorganisms and viruses that may be present on or in a sample. Materials obtained from clinical or forensic settings that contain nucleic acids can also be within the intended meaning of the term "sample." The sample can be a biological sample derived from a human, animal, plant, bacteria or fungi. A sample can originate from a cell, a tissue, and/or an organ. A sample can also be processed samples such as preserved, fixed and/or stabilised samples. A sample can comprise RNA. A sample can comprise DNA.

Kits

The disclosure provides for kits. Kits can comprise reagents for carrying out the methods of the disclosure. Kits can comprise primers of the disclosures (e.g., primers with 5' cleavable ends). A kit can comprise a pool of primers (e.g., random primers). A kit can comprise a target-specific primer. A kit can comprise a pool of different target-specific primers.

A kit can comprise one or more adaptors, polymerases, cleaving agents, and/or ligases. A kit can comprise reagents such as dNTPs and/or NTPs for primer extension. A kit cam comprise a buffer. A buffer can be used for dilution, activation, and/or reconstitution of the items in the kit. The kit can be maintained at room temperature. The kit may be maintained at 4° C. The kit may be frozen.

The kit can comprise instructions for use. Instructions can be written or electronic. The instructions for use can describe how to use the kit in the method of the disclosure. For example, the instructions for use can describe a method of contacting, a sample of single-stranded polynucleotides with a pool of random primers from the kit; extending the primers to generate a first extension product which is hybridized to the single-stranded polynucleotide, thereby generating a first double-stranded duplex; denaturing the double-stranded duplex into its individual strands; hybridizing the pool of primers with the individual first extension product strand; extending the primers to generate a second extension product which is hybridized to the first extension product, thereby creating a second double-stranded duplex; cleaving one or more 5' cleavable ends of the second double-stranded duplex thereby generating one or more nucleotide overhangs; and ligating one or more adaptors to the one or more nucleotide overhangs.

In some instances, the instructions for use can describe a method of contacting a sample of single-stranded polynucleotides with a pool of target-specific primers from the kit; extending the primers to generate a first extension product which is hybridized to the single-stranded polynucleotide, thereby generating a first double-stranded duplex; denaturing the double-stranded duplex into its individual strands; hybridizing the pool of primers with the individual first extension product strand; extending the primers to generate a second extension product which is hybridized to the first extension product, thereby creating a second double-stranded duplex; cleaving one or more 5' cleavable ends of the second double-stranded duplex thereby generating one or more nucleotide overhangs; and ligating one or more adaptors to the one or more nucleotide overhangs, wherein only two steps of extending is performed.

In some instances, the instructions for use can describe a method of contacting a sample of single-stranded polynucleotides with a pool of random primers from the kit; extending the primers to generate a first extension product which is hybridized to the single-stranded polynucleotide, thereby generating a first double-stranded duplex; cleaving one or more 5' cleavable ends of the second double-stranded duplex thereby generating one or more nucleotide overhangs; and ligating one or more adaptors to the one or more nucleotide overhangs, wherein only one round of primer extension is performed.

In some instances, the instructions for use can describe a method of contacting a sample of single-stranded polynucleotides with a pool of random primers from the kit; extending the primers to generate a first extension product which is hybridized to the single-stranded polynucleotide, thereby generating a first double-stranded duplex; denaturing the double-stranded duplex into its individual strands; hybridizing a pool of target-specific primers with the individual first extension product strand; extending the primers to generate a second extension product which is hybridized to the first extension product, thereby creating a second double-stranded duplex; cleaving one or more 5' cleavable ends of the second double-stranded duplex thereby generating one or more nucleotide overhangs; and ligating one or more adaptors to the one or more nucleotide overhangs, wherein only two steps of extending are performed.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

EXAMPLES

Example 1: Single Amplification of DNA

Figure 9:
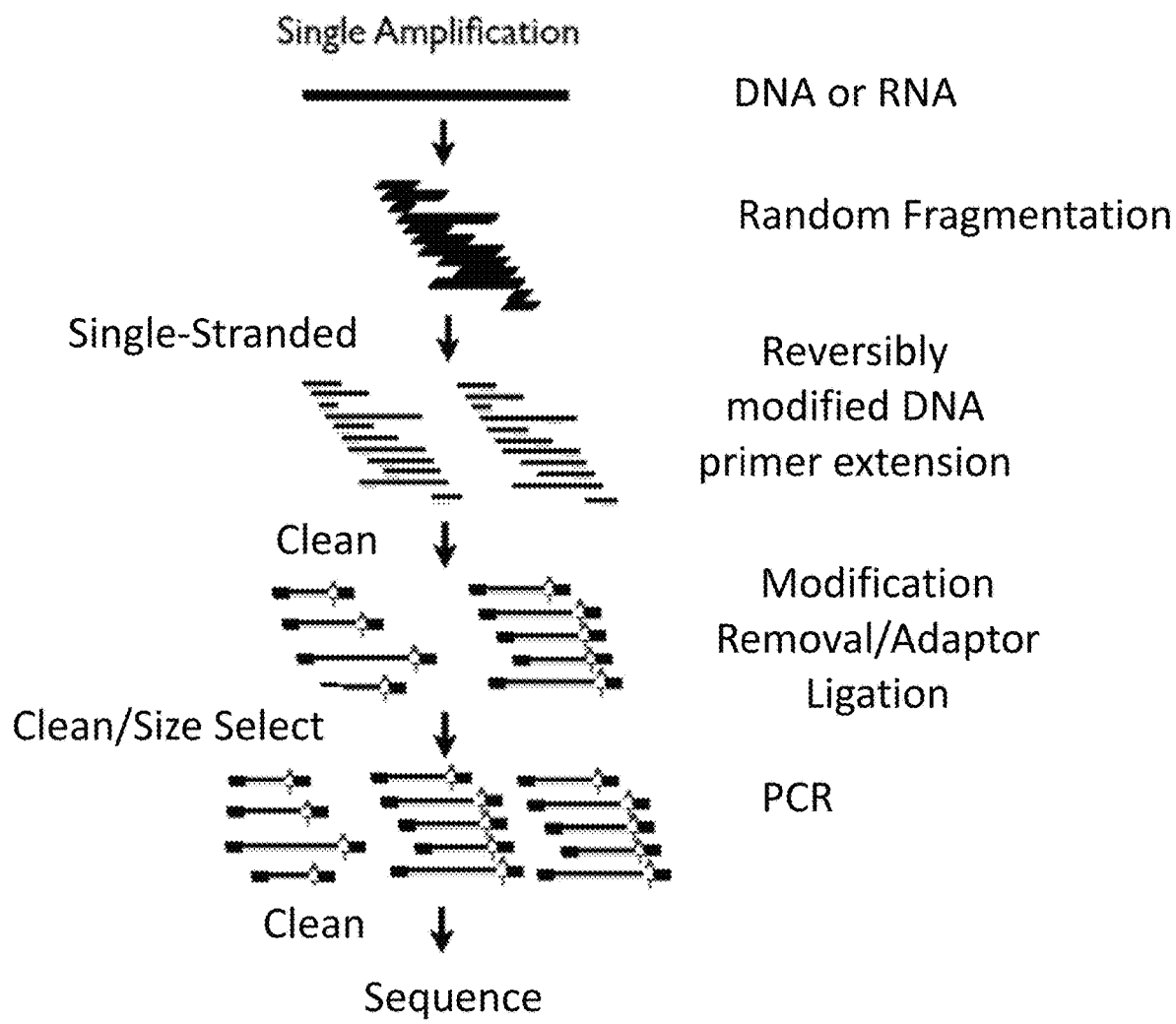
FIG. 9 illustrates a single amplification method of the disclosure.

Genomic DNA is fragmented following standard sample preparation procedures for next generation sequencing. The sample is immediately denatured in the presence of a reversibly modified random hexamer. A mixture of dNTPs (or dNTP's containing dUTP, rA, rU, rG, rC, rUTP, a fluorophore, a dideoxynucleotide, a deoxynucleotide, a radiolabel, or a dye for downstream purification or degradation), polymerase, and buffer are added to the sample. A single extension occurs from the modified hexamer following the incubation time and conditions appropriate for the polymerase. DNA Polymerase I with 5'-3' nuclease activity is used to remove overhangs due to extension past the template molecule. Upon completion of the extension, the sample is purified using standard purification procedures. The sample is then treated to remove the modification (treatment varies depending on modification type) and added to a TA/blunt-end ligation reaction containing modified adaptors (e.g., Illumina adaptors). One adaptor comprises the sequence of the second paired-end adaptor that comprises an overhang that complements the overhang on the extension product. The second adaptor comprises the sequence of the first paired end adaptor that contains a blunt-end which will ligate to the blunt-end of one of the two ends of the extension product. This reaction is then, optionally, size selected and placed directly into an indexing PCR reaction, which is optional depending upon the adaptors that are used. After the optional PCR, the sample is size selected for a size range appropriate for next generation sequencing. An exemplary diagram of the single amplification method of the disclosure is shown in FIG. 9.

Example 2: Double Amplification of DNA

Figure 10:
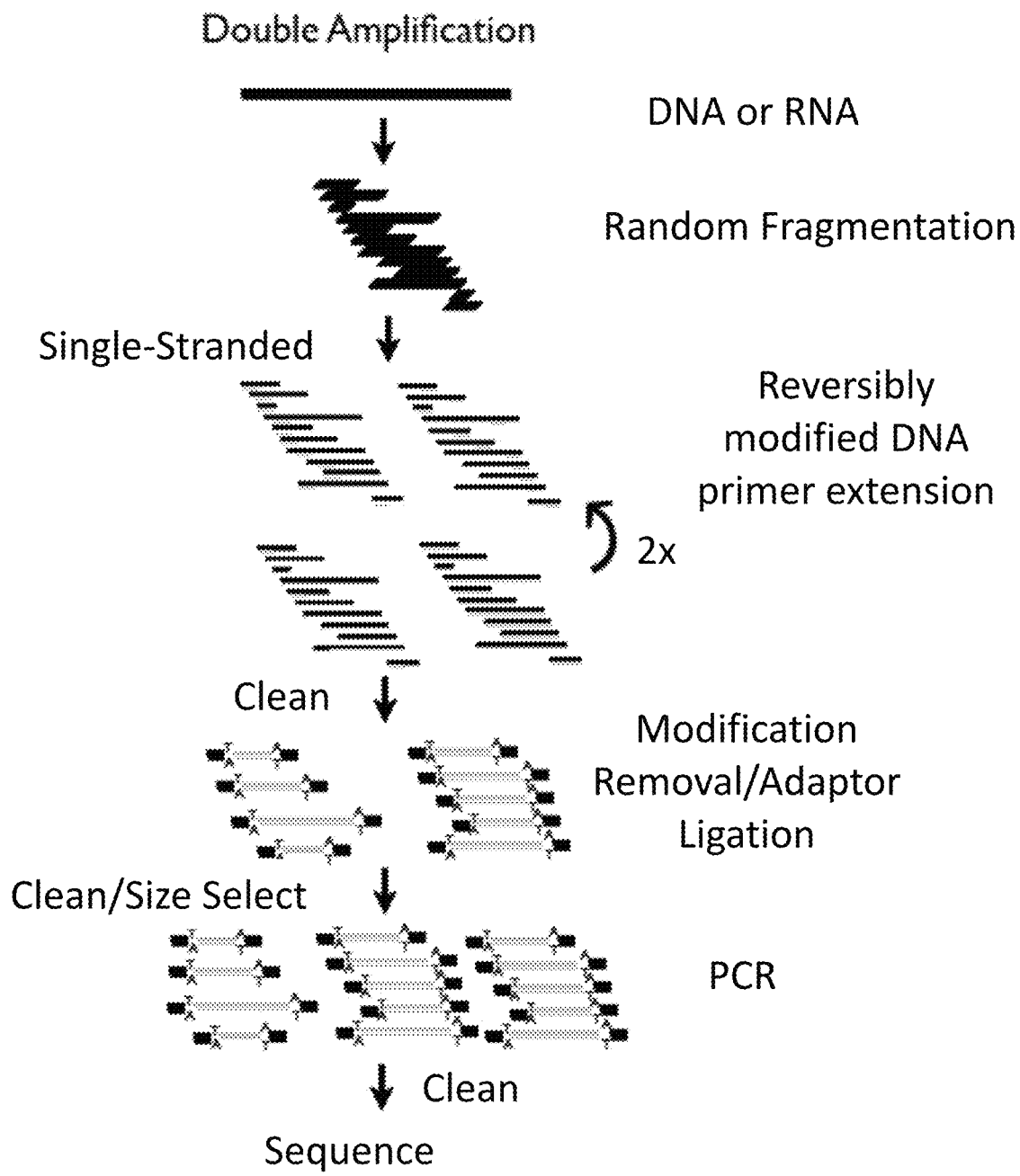
FIG. 10 illustrates a double amplification method of the disclosure.

An exemplary diagram of the single amplification method of the disclosure is shown in FIG. 10. Genomic DNA is fragmented following standard sample preparation procedures for next generation sequencing. The sample is immediately denatured in the presence of a reversibly modified random hexamer. A mixture of dNTPs (or, for example, dNTP's containing dUTP, rA, rU, rG, rC, rUTP, a fluorophore, a dideoxynucleotide, a deoxynucleotide, a radiolabel, or a dye for downstream purification or degradation), polymerase, and buffer are added to the sample. The first extension from the modified hexamer follows the incubation time and conditions appropriate for the polymerase. Once the extension is finished, the sample is denatured and, if necessary, additional polymerase is added to the sample. The second extension follows the same conditions as the first extension. Upon completion of the second extension, the sample is purified using standard purification procedures. The sample is then treated to remove the modification (treatment varies depending on modification type) and added to a TA-ligation reaction containing adaptors (e.g., Illumina adaptors). This reaction is, optionally, size selected and placed directly into an indexing PCR reaction following standard indexing PCR procedures. Alternatively, a non-PCR based approach can be used with altered adaptors. After PCR, the sample is size selected for a size range appropriate for next generation sequencing.

Figure 3:
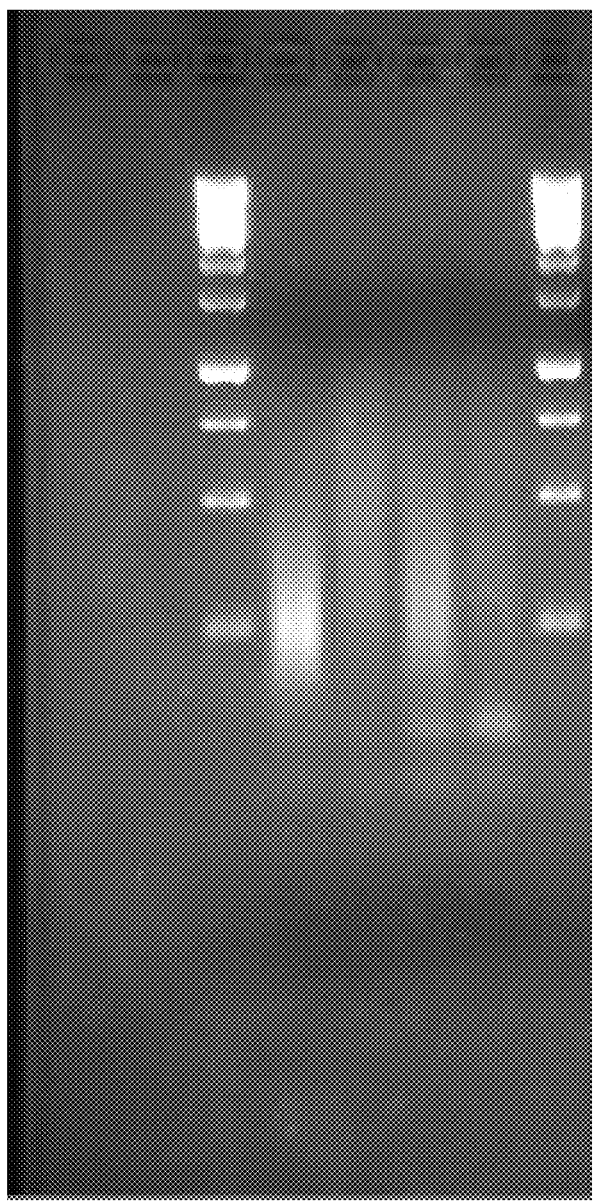
FIG. 3 depicts a 1.5% agarose gel that shows an un-optimized double amplification method of the disclosure.

For example FIG. 3 depicts sample preparation prepared by the double amplification approach. The first lane contains O'GeneRuler 1 kb Plus DNA ladder. The lower brightest band is 500 bp. Bands below correspond to 400, 300, and 200 bp. The second lane shows a test sample that began with 150 ng of DNA. The sample was then treated to produce adapter-ligated nucleic acid fragments using the double amplification method. The third lane began with 75 ng of DNA and was then treated to produce adapter-ligated nucleic acid fragments using the double amplification method. The fourth lane began with 150 ng of DNA and was then treated to produce adapter-ligated nucleic acid fragments using the double amplification method. The fifth lane began with 75 ng of DNA and was then treated to produce adapter-ligated nucleic acid fragments using the double amplification method. The fifth lane is the same ladder used in the first lane. The concentration of each final product after PCR was: Lane 2: 21 ng/µl; Lane 3: 34.3 ng/µl; Lane 4: 25.8 ng/µl; Lane 5: 27.5 ng/µl.

Figure 4:
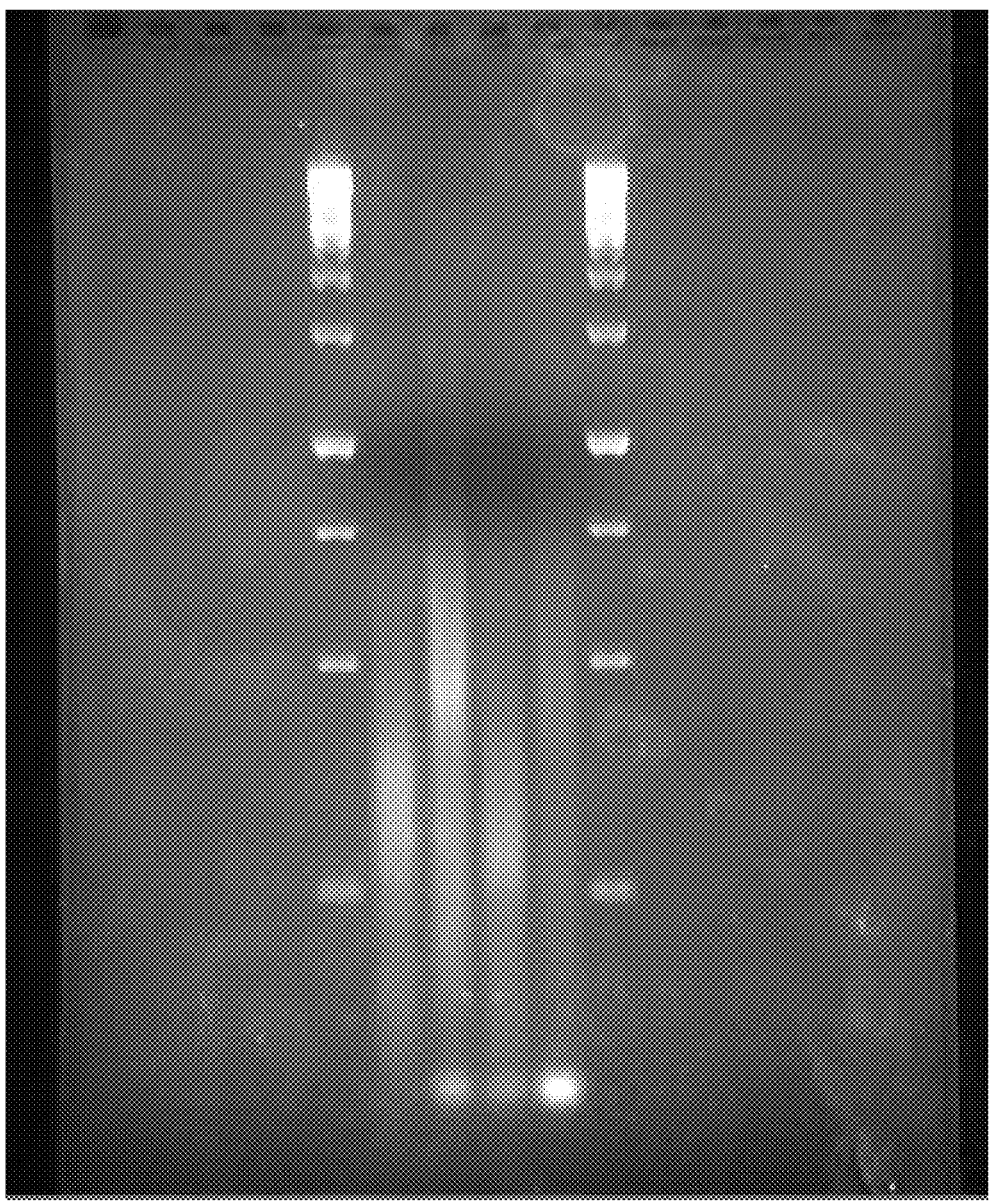
FIG. 4 shows the re-amplification of products from samples in FIG. 3 on a 1.5% agarose gel.

FIG. 4 illustrates the reamplification products from samples of FIG. 3 on a 1.5% agarose gel. In order to remove adaptor-ligated nucleic acid library fragments from the adaptor-adaptor product seen below 200 bp in FIG. 3, the sample was size-selected by gel excision at approximately 220-350 bp, which corresponded to the greatest min. and max. of the brightest size range. The gel excised samples were column purified and used as template for a reamplification PCR reaction. The first lane contains O'GeneRuler 1 kb Plus DNA ladder. The lower brightest band is 500 bp. Bands below correspond to 400, 300, and 200 bp. The second lane shows the re-amplification product of the size-selected product from the second lane of FIG. 3, which began with 150 ng of template that was treated following the double-amplification method. The third lane shows there-amplification product of the size-selected product from the third lane of FIG. 3, which began with 75 ng of template that was treated following the double-amplification method. The fourth lane shows the re-amplification product of the size-selected product from the fourth lane of FIG. 3, which began with 150 ng of template that was treated following the double-amplification method. The fifth lane shows the re-amplification product of the size-selected product from the fifth lane of FIG. 3, which began with 75 ng of template that was treated following the double-amplification method. The sixth lane is the same ladder used in the first lane. Qualitatively, samples appear to amplify after size selection.

Figure 5:
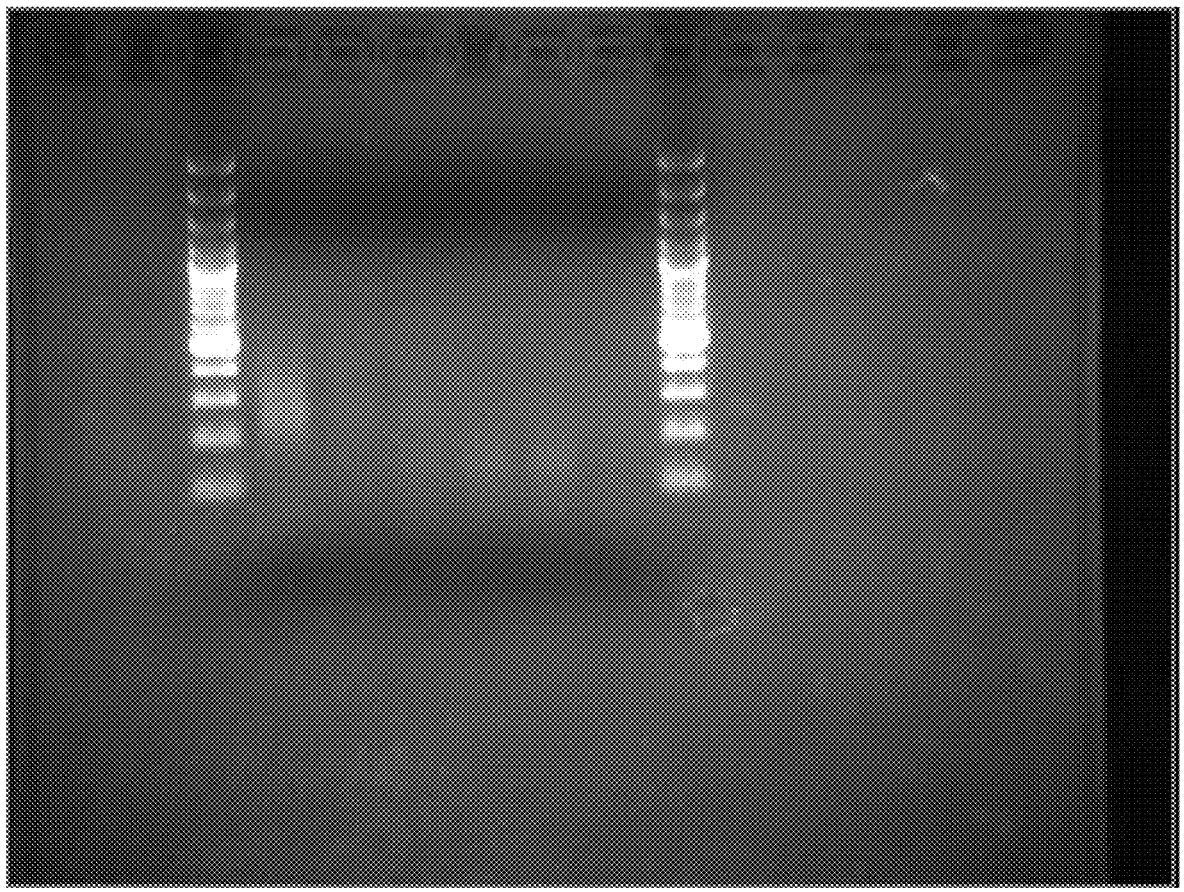
FIG. 5 depicts a 1.5% agarose gel depicting the second replication attempt of the double amplification procedure with appropriate controls.

FIG. 5 depicts a 1.5% agarose gel depicting the second replication attempt of the double amplification procedure with appropriate controls. The first lane contains O'GeneRuler 1 kb Plus DNA ladder. The lower brightest band corresponds to 500 bp. Bands below that correspond to 400, 300, and 200 bp. The second lane shows a test sample that began with 150 ng of DNA. The sample was then treated to produce adapter-ligated nucleic acid fragments using the double amplification method. The third lane was 150 ng DNA that was fragmented but did not undergo the double amplification method and was immediately ran out on an agarose gel. The fourth lane underwent the double amplification method in the absence of DNA and modified hexamer, but contained the Illumina adaptor. The fifth lane underwent the double amplification protocol in the absence of DNA, but contained the modified hexamer and the Illumina adaptor. The sixth lane underwent the double-amplification process, but lacked input DNA and contained adaptor only during the ligation reaction. The seventh lane was a negative control reaction that underwent the double amplification protocol in the absence of any DNA, modified hexamer, and adaptor. The eighth lane is the same as the first lane.

Figure 6:
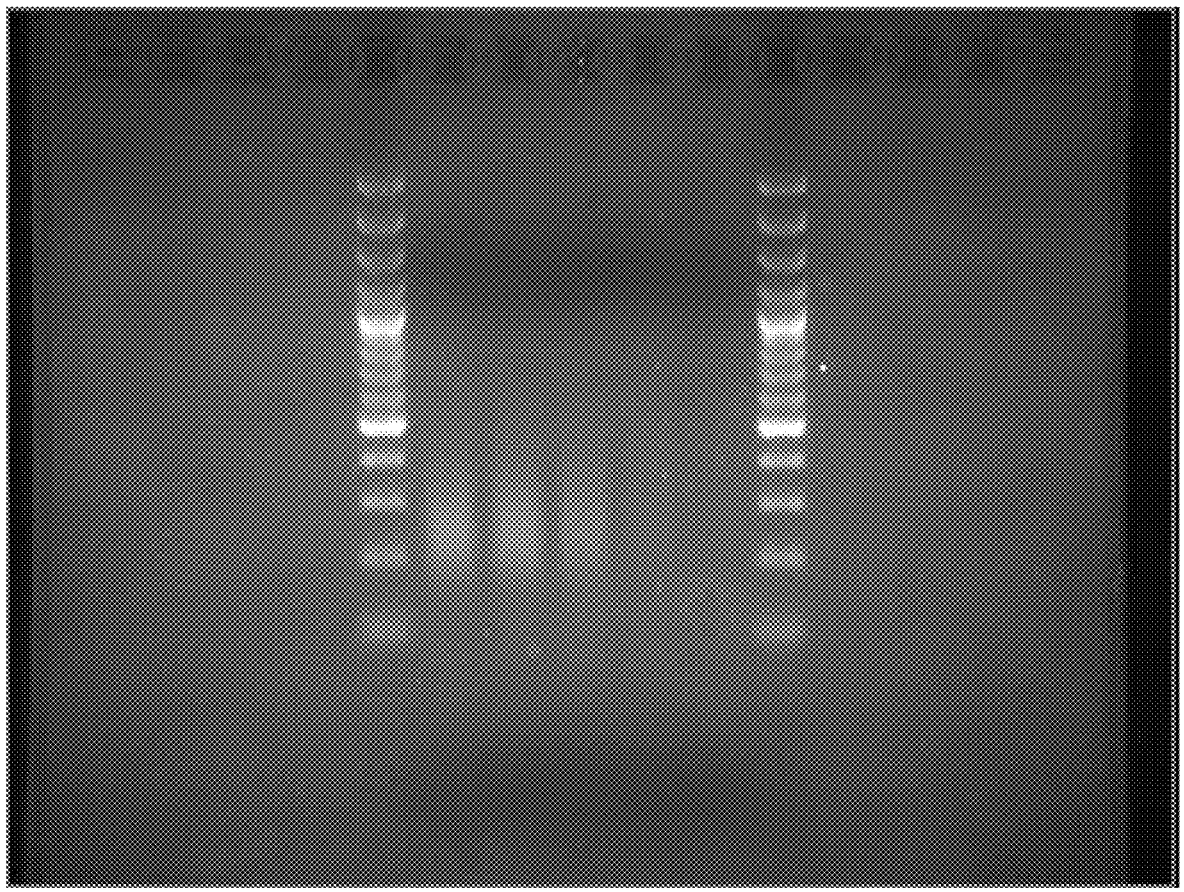
FIG. 6: depicts replication of the double amplification method of the disclosure on a 1.5% agarose gel.

FIG. 6 depicts replication of the procedure conditions in FIG. 3 on a 1.5% agarose gel. The first lane contains O'GeneRuler 1 kb Plus DNA ladder. The lower brightest band corresponds to 500 bp. Bands below that correspond to 400, 300, and 200 bp. The second lane shows a sample that had 150 ng starting DNA. The third lane shows a sample that had 150 bp starting DNA. The fourth lane shows a sample that had 75 ng starting DNA. The fifth lane shows a sample that had 75 ng DNA that was fragmented but did not undergo the double amplification protocol, and was immediately ran out on an agarose gel. The sixth lane was a negative control containing no DNA. The seventh lane was identical to the first lane.

Figure 7:
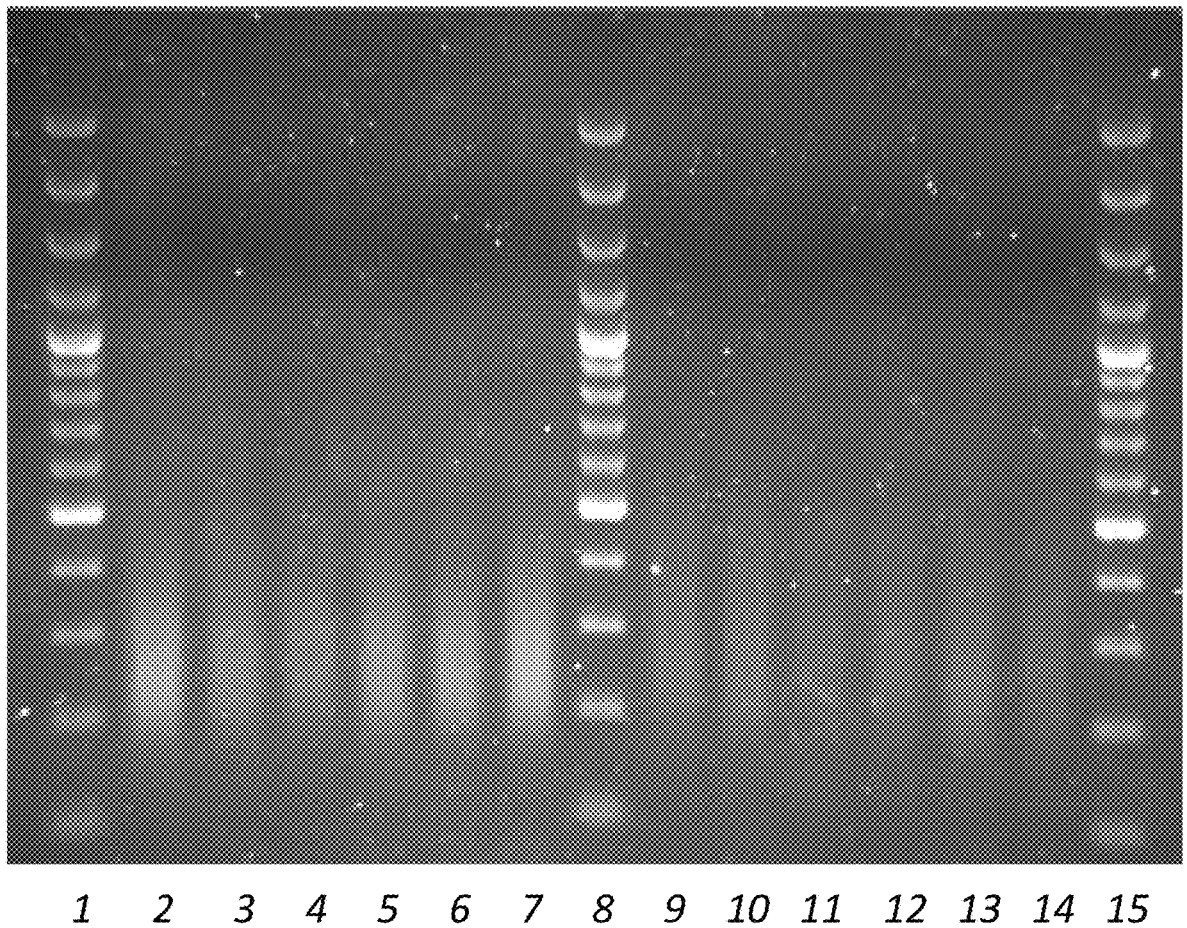
FIG. 7 shows replication of the double amplification method of the disclosure on a 1.5% agarose gel.

FIG. 7 shows replication of the procedure conditions in FIG. 3 on a 1.5% agarose gel. The first lane contains O'GeneRuler 1 kb Plus DNA ladder. The lower brightest band corresponds to 500 bp. Bands below that correspond to 400, 300, and 200 bp. Lanes 2-7 was the product of 150 ng starting DNA that was treated following the double amplification protocol. Lane eight was the same as lane one. Lanes 9-14 was the product of 75 ng starting DNA treated using the double amplification protocol. Lane 15 was the same as lane one. The concentrations of dsDNA products in each lane were quantified using the Qubit HS dsDNA kit and are shown in FIG. 8.

Figure 8:
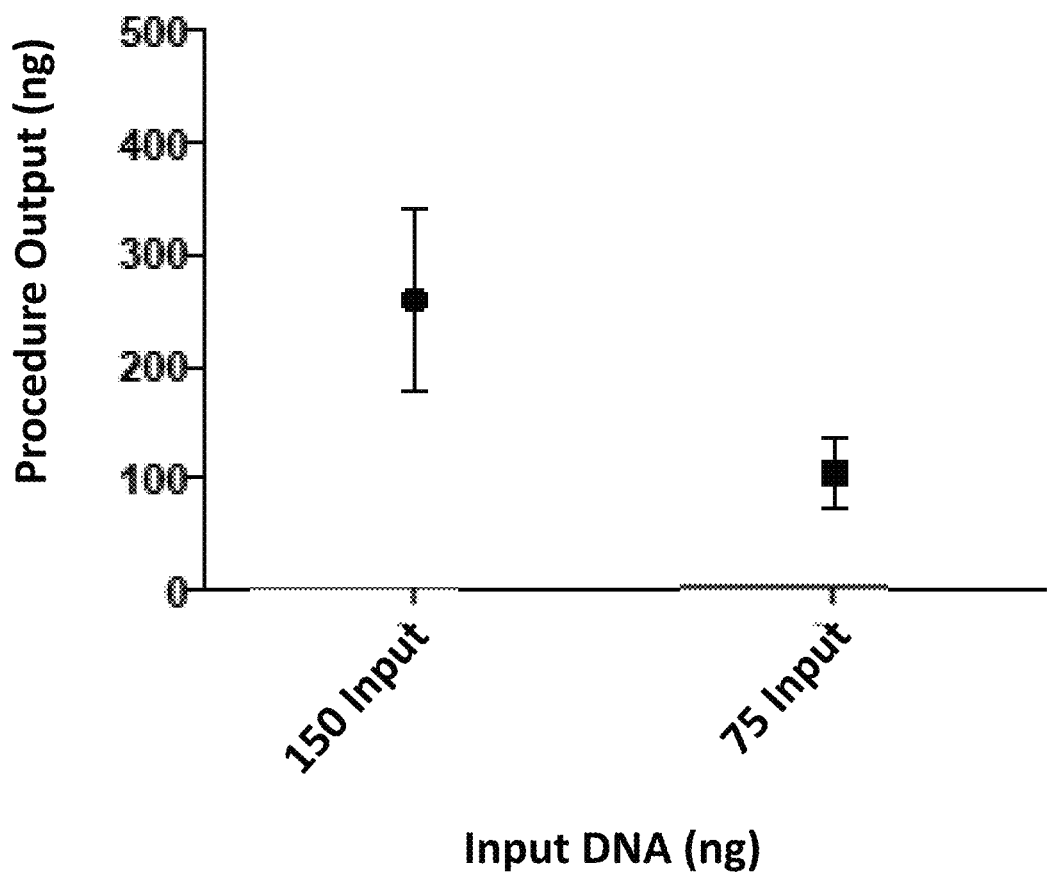
FIG. 8 depicts the replicate results from FIG. 7. The x-axis is the input DNA and the y-axis is the output DNA concentration from the replication experiments. The circle and square shapes represent the average while the bars correspond to the minimum and maximum output range. Circle represents 150 ng of input DNA and square represents 75 ng of input DNA.

FIG. 8 depicts the replicate results from FIG. 7. The x-axis is the input DNA and the y-axis is the output DNA concentration from the replication of the double amplification protocol. The circle and square shapes represent the average while the bars correspond to the minimum and maximum output range. Circle represents the products of 150 ng of input DNA treated following the double amplification protocol and square represents the products 75 ng of input DNA treated following the double amplification protocol.

In order to determine the quantity of DNA capable of successfully generating libraries, 15 ng, 5 ng, and 500 pg of DNA were treated according to the single-amplification method. As measured by Agilent bioanalyzer and qPCR, successful libraries were produced with both the 15-ng and 5-ng samples. The results of the 500-pg sample were inconclusive.

Example 3: Double Amplification of RNA in a Single Reaction Mixture or Vessel mRNA is fragmented following standard sample preparation procedures for next generation sequencing. The sample is immediately denatured in the presence of a reversibly modified random hexamer. A mixture of dNTPs (or, for example, dNTP's containing dUTP, rA, rU, rG, rC, rUTP, a fluorophore, a dideoxynucleotide, a deoxynucleotide, a radiolabel, or a dye for downstream purification or degradation), reverse transcriptase (RT), RNAse inhibitor, and buffer are added to the sample. The first extension from the modified hexamer follows the incubation time and conditions appropriate for the RT. Once the extension is finished, the sample is denatured and quenched, and a polymerase is added to the sample. The second extension follows the conditions that are appropriate for the polymerase. Upon completion of the second extension, the sample is purified using standard purification procedures. The sample is then treated to remove the modification (treatment varies depending on modification type) and added to a TA-ligation reaction containing adaptors (e.g., Illumina). This reaction is, optionally, size selected and placed directly into an indexing PCR reaction following standard indexing PCR procedures. Alternatively, a non-PCR based approach can be used with altered adaptors. After PCR, the sample is size selected for a size range appropriate for next generation sequencing.

Example 4: Double purification Double Amplification of RNA mRNA is fragmented following standard sample preparation procedures for next-generation sequencing. The sample is immediately denatured in the presence of a random hexamer. A mixture of dNTPs, reverse transcriptase (RT), and buffer are added to the sample. The first extension from the hexamer follows the incubation time and conditions appropriate for the RT. Once the extension is finished, the sample is purified following standard procedures. Next, a reversibly modified random hexamer is added to the sample and is denatured and a polymerase is added to the sample. The second extension follows the conditions that are appropriate for the polymerase using dNTPs, dNTPs containing dUTP, rA, rU, rG, rC, rUTP, a fluorophore, a dideoxynucleotide, a deoxynucleotide, a radiolabel, or a dye for downstream purification or degradation. Upon completion of the second extension, the sample is purified using standard purification procedures. The sample is then treated to remove the modification (treatment varies depending on modification type) and added to a TA/blunt-end ligation reaction containing modified adaptors (e.g., from Illumina). One adaptor comprises the sequence of the second paired end adaptor that contains an overhang that complements the overhang on the double extension product. The second adaptor comprises the sequence of the first paired-end adaptor that comprises a blunt-end that can be ligated to the blunt end on one side of the extension product. This reaction is, optionally, size selected and placed directly into an indexing PCR reaction, which is optional depending upon the adaptors that are used. After the optional PCR, the sample is size selected for a size range appropriate for next generation sequencing.

Example 5: Target Amplification with Single Extension with a Reversibly Modified Random Hexamer Primer Genomic DNA is fragmented following standard sample preparation procedures for next generation sequencing. The sample is immediately denatured in the presence of a reversibly modified random hexamer and a mixture of dNTPs (or, for example; dNTPs containing dUTP, rA, rU, rG, rC, rUTP, a fluorophore, a dideoxynucleotide, a deoxynucleotide, a radiolabel, or a dye for downstream purification or degradation), polymerase, and buffer are added to the sample. A single extension occurs from the modified hexamer following the incubation time and conditions appropriate for the polymerase. Upon completion of the extension, the sample is purified using standard purification procedures. The sample is then treated to remove the modification (treatment varies depending on modification type) and added to a TA/blunt-end ligation reaction containing modified adaptors (e.g., Illumina adaptors). One adaptor comprises a modified sequence similar to the second paired end adaptor that comprises an overhang that complements the overhang on the extension product. The second adaptor comprises a modified sequence of the first paired end adaptor that comprises a blunt-end which will ligate to the blunt-end of one of the two ends of the extension product.

If these adaptors are not sufficient for binding to the flow cell for sequencing, an indexing PCR reaction can be performed to incorporate the appropriate sequence. An indexing PCR reaction can be used to tag or barcode samples. The ligation reaction is, optionally, size selected and placed directly into an indexing PCR reaction. This reaction comprises the indexing primer, multiplexing primer, and a target specific primer that comprises the appropriate sequencing oligonucleotide sequence for binding to the flow cell. After the PCR reaction, the sample is size selected for a size range appropriate for next generation sequencing.

Example 6: Alternative Method of Target Amplification with Double Amplification with Reversibly Modified Random Hexamers Genomic DNA is fragmented following standard sample preparation procedures for next generation sequencing. The sample is immediately denatured in the presence of a reversibly modified random hexamer, quenched and a mixture of dNTPs (or, for example, dNTPs containing dUTP, rA, rU, rG, rC, rUTP, a fluorophore, a dideoxynucleotide, a deoxynucleotide, a radiolabel, or a dye for downstream purification or degradation), polymerase, and buffer are added to the sample. The first extension from the modified hexamer follows the incubation time and conditions appropriate for the polymerase. Once the extension is finished, the sample is denatured, quenched, and additional polymerase added to the sample. The second extension follows the same conditions as the first extension. Upon completion of the second extension, the sample is purified using standard purification procedures. The sample is then treated to remove the modification (treatment varies depending on modification type) and added to a TA-ligation reaction containing modified adaptors (e.g., Illumina adaptors).

If these adaptors are not sufficient for binding to the flow cell for sequencing, an indexing reaction can be performed to incorporate the appropriate sequence. The ligation reaction is, optionally, size selected and placed directly into an indexing PCR reaction. This reaction contains the indexing primer, multiplexing primer, and a target specific primer that contains the appropriate oligonucleotide sequence for binding to the flow cell. After PCR, the sample is size selected for a size range appropriate for next generation sequencing.

Figure 11:
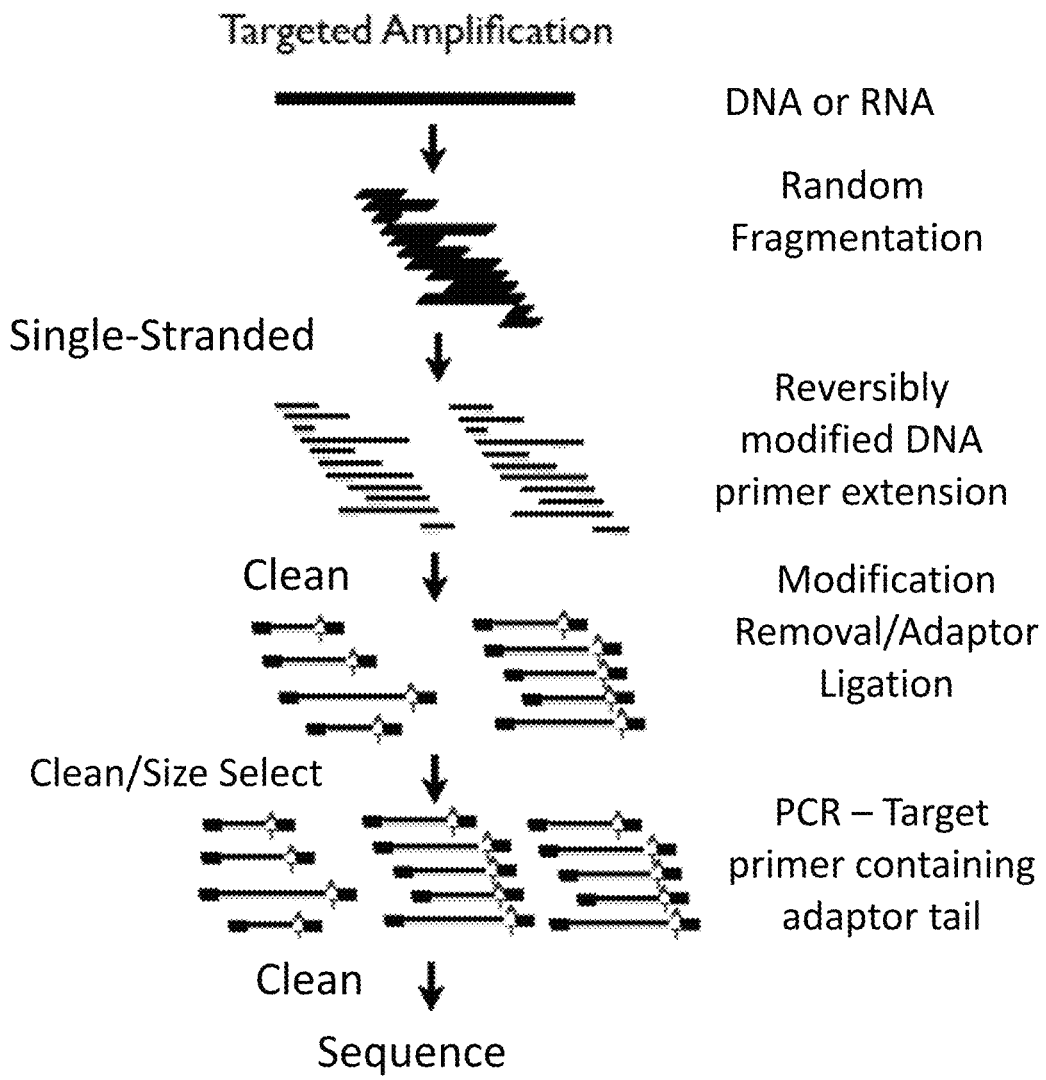
FIG. 11 depicts an exemplary primer extension method of the disclosure.

Example 7: Alternative Method of Target Amplification—Single Amplification with a Reversibly Modified Target Primer An exemplary diagram of the single amplification method of the disclosure is shown in FIG. 11. Genomic DNA is fragmented following standard sample preparation procedures for next generation sequencing. The sample is immediately denatured in the presence of a reversibly modified target primer, quenched and a mixture of dNTPs (or, for example, dNTPs containing dUTP, rA, rU, rG, rC, rUTP, a fluorophore, a dideoxynucleotide, a deoxynucleotide, a radiolabel, or a dye for downstream purification or degradation), polymerase, and buffer are added to the sample. The first extension from the modified target primer follows the incubation time and conditions appropriate for the polymerase. Upon completion of the polymerase extension, the sample is purified using standard purification procedures. The sample is then treated to remove the modification (treatment varies depending on modification type) and added to a TA/blunt-end ligation reaction containing modified adaptors (e.g., Illumina adaptors). One adaptor comprises the sequence of a second paired-end adaptor, such as the second Illumina adapter, that comprises an overhang that complements the overhang on the extension product. The second adaptor comprises the sequence of the first paired-end adaptor, such as the first Illumina adapter, that comprises a blunt-end which will ligate to the blunt-end of one of the two ends of the extension product. This reaction is then, optionally, size selected and placed directly into an indexing PCR reaction, which is optional depending upon the adaptors that are used. After the optional PCR, the sample is size selected for a size range appropriate for next generation sequencing.

Figure 12:
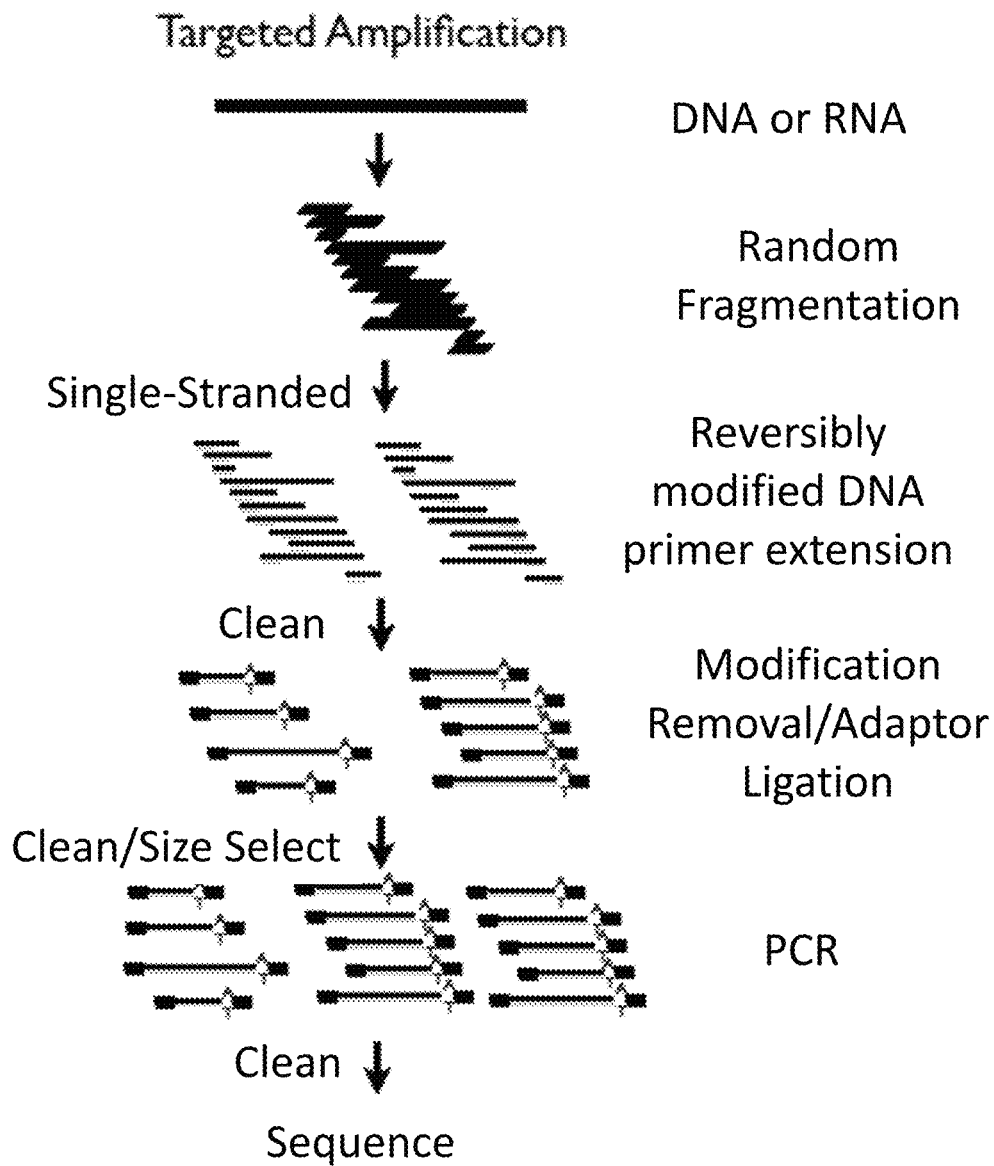
FIG. 12 depicts an exemplary target primer extension method of the disclosure.

Example 8: Alternative Method of Target Amplification—Double Amplification with Reversibly Modified Target Primers An exemplary diagram of the single amplification method of the disclosure is shown in FIG. 12. Genomic DNA is fragmented following standard sample preparation procedures for next generation sequencing. The sample is immediately denatured in the presence of a reversibly modified target primer and a mixture of dNTPs (or dNTPs containing dUTP, rA, rU, rG, rC, rUTP, a fluorophore, a dideoxynucleotide, a deoxynucleotide, a radiolabel, or a dye for downstream purification or degradation), polymerase, and buffer are added to the sample. Once the extension is finished, a modified random hexamer is added to the sample and is denatured, quenched, and additional polymerase is added to the sample. The second extension follows the same conditions as the first extension. Upon completion of the second extension, the sample is purified using standard purification procedures. The sample is then treated to remove the modification (treatment varies depending on modification type) and added to a TA-ligation reaction containing adaptors (e.g., Illumina adaptors). This reaction is, optionally, size selected and placed directly into an indexing PCR reaction following standard indexing PCR procedures. Alternatively, a non-PCR based approach can be used with altered adaptors. After PCR, the sample is size selected for a size range appropriate for next-generation sequencing.

Example 9: Generating Adapters Comprising Overhangs and Random Barcodes

Figure 13:
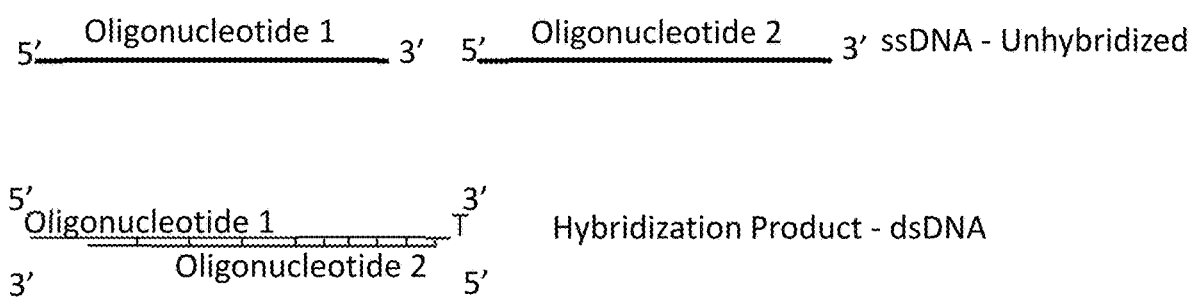
FIG. 13 depicts the generation of adapters by annealing of two single-stranded DNA molecules
Figure 14:
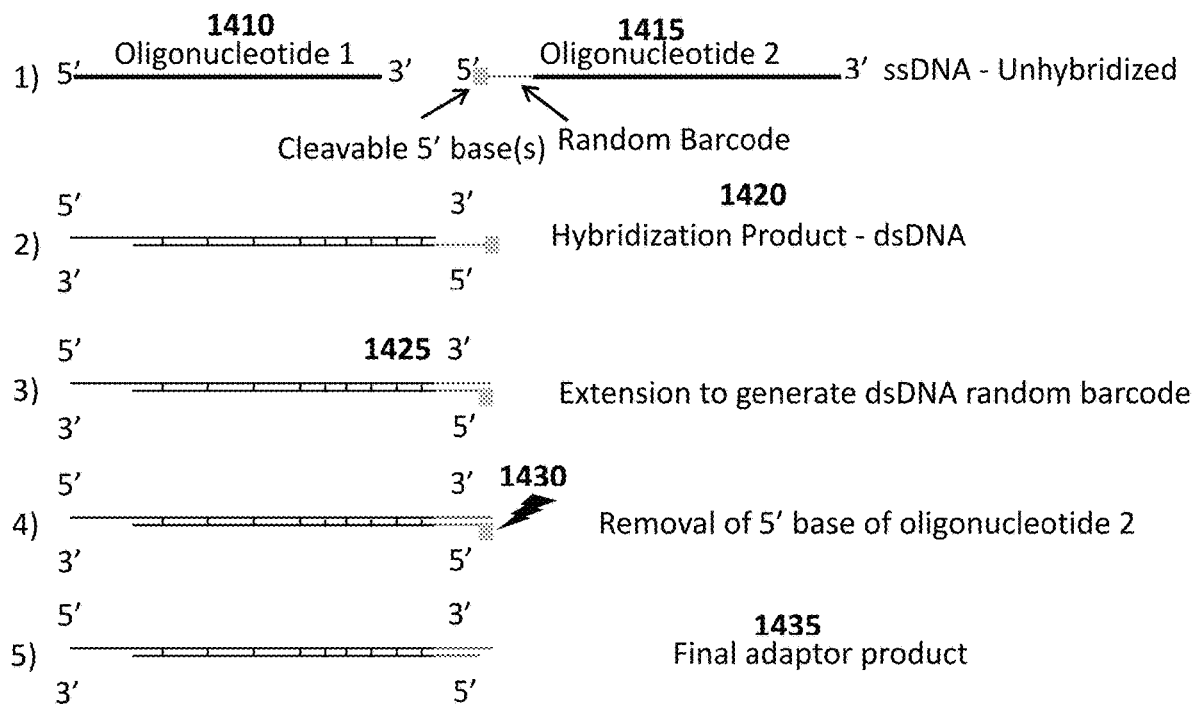
FIG. 14 depicts the generation of adapters containing random barcodes from imperfectly complementary oligonucleotides.
Figure 15:
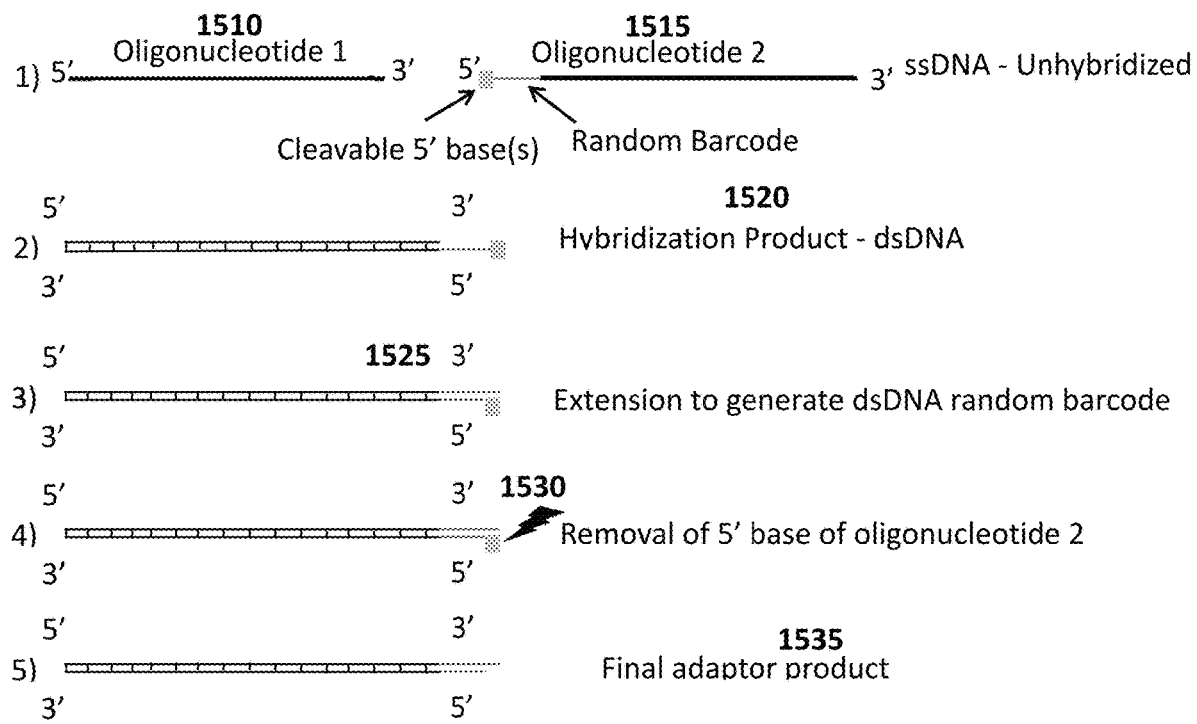
FIG. 15 depicts the generation of adapters containing random barcodes from perfectly complementary oligonucleotides.

FIG. 13 shows a standard method used to form adapters for preparing next-generation sequencing libraries. In FIG. 13, two oligonucleotides comprising complementary sequence are hybridized under selective conditions to produce a double-stranded adapter. FIG. 14 is an exemplary diagram of a method to produce adapters comprising random barcode sequence using the methods of this disclosure. The pool of first oligonucleotides (1410) comprises oligonucleotides that comprise a sequence that is complementary to sequences in the pool of second oligonucleotides (1415). The second oligonucleotides comprise, in addition to said complementary sequence, random nucleotides incorporated by synthesis at their 5' ends, further 5' to which are one or more cleavable nucleotides. Such cleavable nucleotides can be RNA nucleotides. The two pools of oligonucleotides are mixed and allowed to hybridize. The double-stranded product (1420) is treated with dNTPs, buffer, and polymerase in order to extend the first oligonucleotide such that it comprises sequence complementary to the random barcode and the cleavable 5' nucleotide(s) (1425). The cleavable 5' nucleotides, which comprise nucleotides chosen from the group consisting of rU, rA, rC, rG, or dU, are then cleaved (1430). The cleavage is accomplished by treatment with RNaseH or, in the case of dU, by treatment with uracil-DNA glycosylase to generate the final adaptor product (1430), which comprises at least one overhang. FIG. 15 shows the same procedure as FIG. 14, except that Oligonucleotide 2 (1515) comprises the sequence of Oligonucleotide 1 (1510), in addition to which Oligonucleotide 2 only has the additional random barcode and one or more cleavable nucleotides at its 5' end.

Example 10: Preparing Libraries Without Amplification Error

Genomic DNA is fragmented following standard sample preparation procedures for next generation sequencing. The sample is immediately denatured in the presence of a modified random hexamer. A mixture of dNTPs and one or more cleavable dNTPs, polymerase, and buffer are added to the sample. A single extension occurs from the modified hexamer following the incubation time and conditions appropriate for the polymerase. DNA Polymerase I with 5'-3' nuclease activity is used to remove overhangs due to extension past the template molecule. Upon completion of the extension, the sample is treated with a cleaving agent that generates an overhang and cleaves one or more nucleotides within the extended strand. The sample is then purified using standard purification procedures. After treatment and purification, the library comprises single-stranded template sequence with adapter sequences on both ends, while the extended strand is cleaved so that its two ends with adapter sequence are no longer contiguous. The library prepared by this method has no extension or PCR-induced errors, as only the template strand has both adapter sequences necessary for bridge amplification and sequencing.

What is claimed is:

1. A method for generating an adaptor-ligated library of double-stranded nucleic acid molecules in a single reaction vessel or reaction mixture, the method consisting of the following steps:
    (a) generating a plurality of double-stranded nucleic acid molecules from a plurality of single-stranded genomic DNA template polynucleotides by performing a single round of amplification, comprising:
        (i) contacting the plurality of single-stranded genomic DNA polynucleotides with a pool of primers, each primer comprising a cleavable 5' end, and a mixture of dNTPs; and
        (ii) extending the primers by a polymerase with 5' to 3' exonuclease activity to generate a set of polynucleotide extension products that are hybridized to the single-stranded template polynucleotides to form double-stranded nucleic acid molecules having a cleavable 5' end and a blunt end;
    (b) cleaving the cleavable 5' ends of the double-stranded nucleic acid molecules having a cleavable 5' end and a blunt end with a cleaving agent to generate double-stranded nucleic acid molecules having a blunt end, and a 3' overhang end at the cleavage site; and
    (c) ligating to the double-stranded nucleic acid molecules having a blunt end and a 3' overhang end,
        (i) double-stranded nucleic acid adaptors, having a complementary 3' overhang end, to the 3' overhang end of the double-stranded nucleic acid molecules having a blunt end and a 3' overhang end, and
        (ii) double-stranded nucleic acid adaptors, having a blunt end to the blunt end of the double-stranded nucleic acid molecules having a blunt end and a 3' overhang end,
    to generate the adaptor-ligated library of double-stranded nucleic acid molecules.

2. The method of claim 1, wherein the cleavable 5' end is a nucleotide selected from the group consisting of: rA, rC, rG, rU, and dU.

3. The method of claim 1, wherein the pool of primers are random primers.

4. The method of claim 1, wherein the pool of primers are template polynucleotide sequence-specific primers.

5. The method of claim 4, wherein the template polynucleotide sequence-specific primers further comprise a polynucleotide barcode upstream of the sequence-specific nucleotides.

6. The method of claim 1, wherein the cleaving agent is RNase H.

7. The method of claim 1, wherein the polymerase with 5' to 3' exonuclease activity is DNA Polymerase I.

* * * * *